(12) United States Patent
Donaldson

(10) Patent No.: US 10,314,952 B2
(45) Date of Patent: *Jun. 11, 2019

(54) METHOD AND DEVICE FOR SIMULTANEOUSLY DOCUMENTING AND TREATING TENSION PNEUMOTHORAX AND/OR HEMOTHORAX

(71) Applicant: Critical Innovations, LLC, Venice, CA (US)

(72) Inventor: Ross I. Donaldson, Venice, CA (US)

(73) Assignee: Critical Innovations, LLC, Venice, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 15/448,680

(22) Filed: Mar. 3, 2017

(65) Prior Publication Data

US 2017/0182229 A1    Jun. 29, 2017

Related U.S. Application Data

(63) Continuation of application No. 13/961,422, filed on Aug. 7, 2013, now Pat. No. 9,616,203.
(Continued)

(51) Int. Cl.
*A61B 17/34* (2006.01)
*A61M 1/00* (2006.01)
(Continued)

(52) U.S. Cl.
CPC .............. *A61M 1/00* (2013.01); *A61B 17/34* (2013.01); *A61B 17/3415* (2013.01);
(Continued)

(58) Field of Classification Search
CPC ........ A61B 17/3474; A61B 2019/4836; A61B 2019/4873; A61M 1/04; A61M 2039/242; A61M 2210/101; A61M 25/0643
See application file for complete search history.

(56) References Cited

U.S. PATENT DOCUMENTS 3,777,757 A    12/1973 Gray et al.
3,789,852 A    2/1974 Kim et al.
(Continued)

FOREIGN PATENT DOCUMENTS

CN    1756513 B    4/2006
EP    2 168 558 A1    3/2010
(Continued)

OTHER PUBLICATIONS

EP Application No. EP13179479.4, Examination Report dated Oct. 5, 2017, 3 pages.
(Continued)

*Primary Examiner* — Kai H Weng
(74) *Attorney, Agent, or Firm* — Patterson Thuente Pedersen, P.A.

(57) ABSTRACT

A method and device are provided for simultaneously or near-simultaneously diagnosing and treating tension pneumothorax and/or hemothoraxA Veress-type needle portion includes a hollow needle for puncturing the chest wall over a blunt hollow probe biased by one or more springs to extend distally into the pleural cavity. Openings in the blunt hollow probe connect via a pathway to an automatic check valve, which permits the flow of air and/or fluid only in a proximal direction. Pressure from within the pleural cavity is transmitted to the interior surface of a pressure documenter. If pressure greater than atmospheric pressure is present in the pleural cavity, the pressure documenter will be automatically urged proximally to simultaneously allow air and/or fluid to escape from the pleural space through the device, thus treating the tension pneumothorax and/or hemothorax, as well as providing a stable indicator to positively document the diagnosis of increased pressure.

11 Claims, 18 Drawing Sheets

Related U.S. Application Data

(60) Provisional application No. 61/680,505, filed on Aug. 7, 2012.

(51) Int. Cl.
*A61M 27/00* (2006.01)
*A61M 1/04* (2006.01)
*A61M 25/06* (2006.01)
*A61M 39/24* (2006.01)
*A61B 90/00* (2016.01)

(52) U.S. Cl.
CPC .......... *A61B 17/3474* (2013.01); *A61M 1/04* (2013.01); *A61M 25/0606* (2013.01); *A61M 27/00* (2013.01); *A61B 17/3496* (2013.01); *A61B 2090/0807* (2016.02); *A61B 2090/0814* (2016.02); *A61M 25/0643* (2013.01); *A61M 2039/242* (2013.01); *A61M 2205/3331* (2013.01); *A61M 2210/101* (2013.01)

(56) References Cited

U.S. PATENT DOCUMENTS

| | | |
|---|---|---|
| 3,894,540 A | 7/1975 | Bonner, Jr. |
| 4,153,058 A | 5/1979 | Nehme |
| 4,164,938 A | 8/1979 | Patton |
| 4,221,215 A | 9/1980 | Mandelbaum |
| 4,392,853 A | 7/1983 | Muto |
| 4,617,011 A | 10/1986 | Bloxom, Jr. |
| 4,664,660 A | 5/1987 | Goldberg et al. |
| 4,767,409 A | 8/1988 | Brooks |
| 4,767,411 A | 8/1988 | Edmunds |
| 4,944,724 A | 7/1990 | Goldberg et al. |
| 5,098,388 A | 3/1992 | Kulkashi et al. |
| 5,207,647 A | 5/1993 | Phelps |
| 5,215,522 A | 6/1993 | Page et al. |
| 5,215,531 A | 6/1993 | Maxson et al. |
| 5,242,398 A | 9/1993 | Knoll et al. |
| 5,256,148 A | 10/1993 | Smith |
| 5,263,939 A | 11/1993 | Wortrich |
| 5,284,474 A | 2/1994 | Adair |
| 5,300,046 A | 4/1994 | Scarfone et al. |
| 5,334,159 A | 8/1994 | Turkel |
| 5,336,193 A | 8/1994 | Rom et al. |
| 5,376,082 A | 12/1994 | Phelps |
| 5,421,821 A | 6/1995 | Janicki |
| 5,429,608 A | 7/1995 | Rom et al. |
| 5,478,333 A | 12/1995 | Asherman, Jr. |
| 5,514,111 A | 5/1996 | Phelps |
| 5,520,650 A | 5/1996 | Zadini et al. |
| 5,545,179 A | 8/1996 | Williamson, IV |
| 5,660,883 A | 8/1997 | Omura |
| 5,662,616 A | 9/1997 | Bousquet |
| 5,685,852 A | 11/1997 | Turkel et al. |
| 5,725,506 A | 3/1998 | Freeman et al. |
| 5,807,341 A | 9/1998 | Heim |
| 5,827,221 A | 10/1998 | Phelps |
| 5,897,531 A | 4/1999 | Amirana |
| 5,902,273 A | 5/1999 | Yang et al. |
| 5,997,486 A | 12/1999 | Burek et al. |
| 6,019,735 A | 2/2000 | Kensey et al. |
| 6,221,048 B1 | 4/2001 | Phelps |
| 6,402,770 B1 | 6/2002 | Jessen |
| 6,447,483 B1 | 9/2002 | Steube et al. |
| 6,605,063 B2 | 8/2003 | Bousquet |
| 6,638,253 B2 | 10/2003 | Breznock |
| 6,770,070 B1 | 8/2004 | Balbierz |
| 6,905,484 B2 | 6/2005 | Buckman et al. |
| 7,135,010 B2 | 11/2006 | Buckman et al. |
| 7,229,433 B2 | 6/2007 | Mullen |
| 7,244,245 B2 | 7/2007 | Purow et al. |
| 7,429,687 B2 | 9/2008 | Kauth et al. |
| 7,615,674 B2 | 11/2009 | Asherman |
| 7,789,873 B2 | 9/2010 | Kubalak et al. |
| 7,811,293 B2 | 10/2010 | Simpson et al. |
| 7,824,366 B2 | 11/2010 | Tanaka |
| 7,842,058 B2 | 11/2010 | Simpson et al. |
| 8,057,443 B2 | 11/2011 | McNeil |
| 8,062,315 B2 | 11/2011 | Aster et al. |
| 8,128,648 B2 | 3/2012 | Hassidov et al. |
| 8,430,094 B2 | 4/2013 | Tanaka et al. |
| 8,518,053 B2 | 8/2013 | Tanaka et al. |
| 9,616,203 B2 | 4/2017 | Donaldson |
| 2003/0073960 A1 | 4/2003 | Adams et al. |
| 2003/0233073 A1 | 12/2003 | Purow et al. |
| 2004/0078026 A1 | 4/2004 | Wagner |
| 2004/0133226 A1 | 7/2004 | Buckman et al. |
| 2006/0025723 A1 | 2/2006 | Ballarini |
| 2007/0021768 A1 | 1/2007 | Nance et al. |
| 2007/0038180 A1 | 2/2007 | Sinha et al. |
| 2008/0103451 A1 | 5/2008 | Schaefer, Jr. et al. |
| 2008/0125750 A1 | 5/2008 | Gaissert |
| 2008/0312638 A1 | 12/2008 | McNeil |
| 2009/0005800 A1 | 1/2009 | Franer et al. |
| 2009/0205646 A1 | 8/2009 | Tanaka et al. |
| 2009/0205651 A1 | 8/2009 | Tanaka et al. |
| 2009/0318898 A1 | 12/2009 | Dein |
| 2010/0170507 A1 | 7/2010 | Tanaka et al. |
| 2010/0204707 A1 | 8/2010 | Tanaka et al. |
| 2011/0054340 A1 | 3/2011 | Russ et al. |
| 2011/0152874 A1 | 6/2011 | Lyons |
| 2012/0051967 A1 | 3/2012 | Murphy et al. |
| 2012/0191044 A1 | 7/2012 | Koike |
| 2012/0209166 A1 | 8/2012 | Power et al. |
| 2013/0131645 A1 | 5/2013 | Tekulve |
| 2014/0046303 A1 | 2/2014 | Donaldson |
| 2015/0182733 A1 | 7/2015 | Donaldson |

FOREIGN PATENT DOCUMENTS

| | | |
|---|---|---|
| GB | 2140301 A | 11/1984 |
| WO | WO 2008/029109 A1 | 3/2008 |

OTHER PUBLICATIONS

Mabry et al., "Prehospital advances in the management of severe penetrating trauma," Crit Care Med 2008, vol. 36, No. 7 (Suppl.), 9 pages.

Leigh-Smith et al., "Tension pneumothorax—time for a re-think?" Emerg Med J 2005, vol. 22, pp. 8-16.

Maxwell et al., "The Hanging Drop to Locate the Pleural Space: A Safer Method for Decompression of Suspected Tension Pneumothorax?," The Journal of Trauma, Injury, Infection, and Critical Care, vol. 69, No. 4, Oct. 2010, 2 pages.

Bassett et al., "Design of a mechanical clutch-based needle-insertion device," PNAS Early Edition, Aug. 25, 2008, 6 pages.

EP Application No. 13179479.4, Examination Report dated Feb. 7, 2017, 3 pages.

EP Application No. 14200292.2, Search Report dated May 22, 2015, 8 pages.

EP Application No. EP 13179479.4, Search Report dated Nov. 8, 2013, 5 pages.

Application and File History for U.S. Appl. No. 13/961,422, filed Aug. 7, 2013. Inventor: Donaldson.

Application and File History for U.S. Appl. No. 14/581,339, filed Dec. 23, 2014. Inventor: Donaldson.

METHOD AND DEVICE FOR SIMULTANEOUSLY DOCUMENTING AND TREATING TENSION PNEUMOTHORAX AND/OR HEMOTHORAX

RELATED APPLICATION

This application is a continuation of U.S. application Ser. No. 13/961,422 filed Aug. 7, 2013, which claims the benefit of U.S. Provisional Application No. 61/680,505 filed Aug. 7, 2012, which is incorporated herein in its entirety by reference.

FIELD OF THE INVENTION

The present invention relates to devices and methods for treating patients suffering from closed tension pneumothorax and/or hemothorax. In particular, the present invention relates to devices and methods for treating patients suffering from tension pneumothorax and/or hemothorax that substantially reduce the possibility of iatrogenic lung puncture and/or introduction of air into the pleural space, while swiftly allowing for the simultaneous documentation and treatment of these life-threatening conditions.

BACKGROUND OF THE INVENTION

Normally, the lungs are kept inflated within the chest cavity by negative pressure in the pleural spaces. A lung will partially or completely collapse if air and/or blood collects in the pleural space, thus causing loss of negative pressure (termed pneumothorax and/or hemothorax respectively). The most dangerous type of these conditions is tension pneumothorax (i.e. pressure pneumothorax or valve pneumothorax) and/or, less commonly, tension hemothorax. In this case, the lung not only fully collapses, but the air and/or fluid within the pleural space builds up enough pressure in the chest cavity to cause a significant decrease in the ability of the body's veins to return blood to the heart, which can result in cardiac arrest and death unless treated emergently.

Tension pneumothorax and/or hemothorax is the second leading cause (33%) of potentially preventable combat deaths and constitutes around 5% of all fatal military injuries. In addition to penetrating and blast trauma, tension pneumothorax can also occur from other forms of barotrauma, such as high pressures during mechanical ventilation, underlying lung disease (e.g. asthma, emphysema, blebs), changes in environmental pressure (e.g. hyperbaric treatment, high-altitude, rapid ascent from scuba diving), and/or Cardio-Pulmonary Resuscitation (CPR). Studies on ICU deaths show rates of undiagnosed tension pneumothorax ranging from 1.1% to 3.8%, with increased risk for patients who had ventilation or cardiopulmonary resuscitation. Early diagnosis and swift treatment of tension pneumothorax and/or hemothorax, by relieving the pressure in the pleural space, is critical for patient survival. However, correct diagnosis of this condition is far from guaranteed during emergencies. Presentation of the classic signs and symptoms are highly variable and, in many cases, the time and/or treatment environment does not permit diagnostic confirmation by chest x-ray, ultrasound, or other means. Thus, current treatments may be withheld due to fear of causing patient harm or, conversely, may be inadvertently performed on a healthy lung and worsen the patient's condition.

Traditional treatment, especially in the out-of-hospital emergency arena, is to place a wide-bore needle and plastic cannula into the chest cavity to release pressure (i.e. "needle thoracostomy" or "chest decompression"). For example, current Tactical Combat Casualty Care guidelines recommend the consideration of this "needle decompression" in casualties with chest trauma and progressive respiratory distress. Simple wide-bore needles for this use are widely available commercially. Examples include standard IV catheters in various sizes (e.g. from BD Angiocath™) and the "H&H Tension Pneumothorax Needle" from H&H Associates, Inc. However, although standard needle decompression is an effective treatment for pressure buildup, it has multiple disadvantages. Such treatment results in lung compromise, as an open passage is left in the chest wall producing a non-tension open pneumothorax; possible iatrogenic injury to the lung or heart, from introduction of the sharp needle tip; the necessity of all patients having subsequent tube thoracostomy (a major procedure), upon presentation to a higher level of care; and, inability to perform the technique bilaterally, without subsequent continuous positive pressure ventilation (because both lungs are deflated).

Some authors have discussed solutions for individual improvements upon this simple needle thoracostomy technique, including the use of a syringe filled with sterile saline attached to the cannula or the "hanging drop" technique to help confirm pleural penetration; an Asherman chest seal to stabilize the cannula and provide a check valve; or, the attachment of a flutter valve to the cannula to decrease the chances of iatrogenic pneumothorax (e.g. Cook® Emergency Pneumothorax, Pre-Hospital Emergency Pneumothorax, and Spec Ops Emergency Pneumothorax Sets). However, these advances all have individual drawbacks, take additional steps and equipment, and are not common in actual use.

The literature discloses various additional known methods and devices related to the treatment of tension pneumothorax and/or hemothorax.

For example, U.S. Pat. No. 2012/0051967 A1 to Murphy et al describes a battlefield needle container for carrying a standard needle to be used for treating tension pneumothorax and/or hemothorax. However, this device has no improvements upon the needle device itself.

U.S. Pat. No. 5,478,333 to Asherman, Jr. discloses a medical dressing for treatment of open chest injuries. The device consists of a dressing made of pliable plastic placed over an open wound, having a check valve to allow built up pressure to vent. Similar devices and procedures are set forth in U.S. Pat. No. 7,429,687 B2 to Kauth et al, U.S. Pat. No. 7,615,674 B2 to Asherman, and 2011/0054340 to Russ et al. Although these and similar works are capable of preventing the conversion of an open pneumothorax to a tension pneumothorax, all such devices are incapable of treating a closed tension pneumothorax, as they have no means to penetrate the chest and allow the built up pressure to vent. Additionally, when used over a standard needle, they have multiple disadvantages including a multi-step process, which at the minimum results in a transient open pneumothorax, as well as the lack of any documentation means.

U.S. Pat. No. 4,164,938 to Higaki, et al describes a simple one-stage device for the diagnosis of tension pneumothorax. This work describes a standard needle attached to a balloon; when inserted into the pleural space, the balloon inflates if there is increased pressure, transiently indicating tension. However, although this medical pressure-gauge device can diagnose tension pneumothorax, it is not a treatment device as no air (besides that inside the balloon) is actually released from the body. Additionally, it has the added disadvantage of a sharp distal needle end, which may potentially injure the lung.

U.S. Pat. No. 4,153,058 to Nehme discloses a pleural decompression catheter for releasing entrapped air within a human body. The device consists of an elongated prong inserted into the chest, having a passage for establishing communication from the pleural space, through a one-way balloon valve, to the external environment. Once the device is inserted into the patient, the trocar is removed to release trapped air. However, this device, as well as a similar one disclosed in U.S. Pat. No. 4,664,660 to Goldberg et al, has numerous disadvantages for the emergent treatment of tension pneumothorax and/or hemothorax. The size and complexity of these devices render them ill-suited for use in emergency situations. Additionally, both devices are placed over a trocar, necessitating a multi-step process for treatment. They additionally have no means to affix to the patient, in case of transport, and have no documentation means, to alert later caregivers that tension had (or had not) previously been present. Additionally, both have sharp distal ends which may injure the lung upon initial placement, especially if a pneumothorax and/or hemothorax was incorrectly diagnosed.

U.S. Pat. No. 7,229,433 to Mullen describes an apparatus specifically for treating pneumothorax and/or hemothorax. This involves the introduction of a catheter with a check valve over a large trocar obturator unit, along with a means of securely affixing the catheter to the patient. However, this device has similar disadvantages, including the risk of lung injury upon introduction of the trocar into the chest cavity, especially if a pneumothorax and/or hemothorax was incorrectly diagnosed. Furthermore, the device requires a multi-step process for treatment (adding complexity and delay) and lacks a diagnostic documentation indicator to alert current and later caregivers of the diagnosis.

U.S. Pat. No. 6,402,770 to Jessen describes a method and apparatus for placing a tube into the body that can also be used for the treatment of pneumothorax and/or hemothorax. It utilizes a cam action dual-blade thoracostomy device that additional has a check valve component. However, this device has the disadvantage of possible injury to the chest wall neurovascular structures, the lung, and other organs through the use of moving blades. It also lacks a diagnostic documentation indicator.

Similarly, U.S. Pat. Application No. 2008/0312638 and U.S. Pat. No. 8,057,443 B2 to McNeil describe an apparatus for withdrawing fluid and/or air from a space in the body that could be used for treatment of tension pneumothorax. The work includes a catheter that is placed over a hollow needle into the pleural space with means for affixing said device to the patient and withdrawing air and/or fluid. However, this device has similar disadvantages for the emergency treatment of pneumothorax and/or hemothorax, including the aforementioned disadvantages to Mullen's as well as the lack of an automatic check valve.

Similarly, U.S. Pat. No. 4,944,724 to Goldberg, et al describes an apparatus for locating a body cavity having a fluctuating fluid pressure, such as fluid in the pleural space. The work includes a catheter that is placed over a hollow trocar with a pressure bubble indicator, to allow for visualization of changes in pressure while placing the needle, and a means for affixing the device to the patient. However, the apparatus is not fashioned specifically for the emergent treatment of tension pneumothorax and/or hemothorax, and thus has multiple disadvantages for this indication. The device overall is bulky and requires a multi-step introduction of a sharp trocar, which may potentially injure the lung. Furthermore, its indicator is transient and does not leave stable documentation of tension for later caregivers to view.

Additionally, U.S. Pat. No. 6,770,070 to Balbierz describes a method and apparatus for the prevention of pneumothorax during lung biopsy, which can seal lacerations in the lung. However, this device is not for the emergent treatment of tension pneumothorax and/or hemothorax.

Also known in the art are "Veress" or "Veress-type" needles, which have an outer needle having a sharp distal end and an inner probe with a blunt distal end that extends through the outer needle. In Veress needles, the inner probe is biased to force the blunt distal end of the probe beyond the sharp distal end of the outer needle. This then prevents injury to internal organs (e.g. lung). However, when the blunt distal end of the probe encounters dense material (e.g. chest wall), the probe is forced backward, and the sharp end of the needle is presented so that it can puncture the dense material.

Most Veress needles in the art describe use primarily for abdominal laparoscopic procedures, such as U.S. Pat. Nos. 5,376,082; 5,207,647; 5,514,111; 5,827,221; and 6,221,048 to Phelps; U.S. Pat. No. 5,660,883 to Scarfone, et al; 2009/0005800 to Franer et al, and U.S. Pat. No. 5,098,388 to Kulkashi et al. These are not adapted for the emergent treatment of pneumothorax and/or hemothorax and thus have multiple disadvantages in being modified to do so, including being overly large and bulky for emergency use, lacking an automatic check valve to prevent introduction of external air, and the absence of a documentation indicator to alert later caregivers that tension of pneumothorax and/or hemothorax had previously been treated and thus necessitating further care.

Similarly, U.S. Pat. No. 5,421,821 to Janicki et al describes a Veress needle system and method for insufflating the abdominal cavity prior to laparoscopic surgery. This system includes an electronic sensor to detect negative pressure and indicate when the surgeon enters the abdominal cavity. However, this device is not adapted for the emergent diagnosis and treatment of pneumothorax and/or hemothorax. It lacks an automatic check valve to prevent introduction of external air and has no means to affix to the device to the patient. Additionally, the electronic pressure indicator described only indicates negative (not positive "tension") pressure and is a transient (not stable) indicator.

U.S. Pat. No. 5,300,046 to Scarfone, et al; U.S. Pat. No. 5,997,486 to Burek, et al; and, U.S. Pat. No. 5,725,506 to Freeman, et al describes similar devices and methods for thoracentesis; a Veress needle inserted into the pleural space is used to introduce a catheter for drainage. Although these devices could be used to relieve a tension pneumothorax, they have multiple disadvantages in the emergent setting including the need for a multi-step process requiring withdrawal of the needle from a catheter and the lack of a stable documentation indicator, to alert later caregivers that tension pneumothorax and/or hemothorax had previously been treated thus necessitating further care.

U.S. Pat. No. 5,334,159 to Turkel describes a Veress thoracentesis needle having a direct passageway through the needle for withdrawing fluid (no overlying catheter) and an automatic check valve to prevent introduction of air into the pleural space. Although this device is a significant improvement over prior art, it is fashioned for standard pleural fluid withdrawal, not for the emergent treatment of tension pneumothorax and/or hemothorax. Thus it has multiple disadvantages in being used for the later indication in the emergency arena. This includes the absence of a diagnostic documentation indicator to alert later caregivers that a tension pneumothorax had been treated prior to arrival. If this device was used in an out-of-hospital emergency (e.g. in an ambulance or battlefield), the only way of knowing that a tension pneumothorax had been treated would be by the out-of-hospital provider hearing a short "whish" of air out of the needle, something that can be very subjective and difficult to hear in a loud out-of-hospital environment with possible sirens and/or gunfire. Thus, without the stable indicator, each patient that had needle decompression performed in the field (whether or not they truly had a tension pneumothorax at that time) would likely need a full chest tube thoracostomy upon arrival to higher care. This is because both patients who actually had a tension pneumothorax and those who had been misdiagnosed could both have the same diagnostic findings upon later chest x-ray or ultrasound (i.e. a (re)inflated lung due to the automatic check valve venting air). Thus, it is dangerous to remove the device without placing a full chest tube as tension pneumothorax could rapidly return.

Turkel also describes no means to affix the device to the patient, to ensure that the catheter is not prematurely removed. Although not necessary for simple in-hospital thoracentesis as described in the work, a sturdy means of affixing the device to the patient is critical in the emergent arena (both in- and out-of-hospital), when the patient may be undergoing rapid transport and/or significant other movement, such as from concurrent Cardio-Pulmonary Resuscitation (CPR) or surgery.

Additionally, Turkel describes subsequent modifications in U.S. Pat. No. 5,685,852, which is a similar Veress device modified for use as an epidural needle. This device has an indicator to allow visualization of the rotation of the needle, but if used for the treatment of tension pneumothorax and/or hemothorax would have similar disadvantages as aforementioned.

U.S. Pat. No. 6,447,483 to Steube, et al is a Veress thoracentesis needle similar to that of Turkel, with an improved hyper-sensitive detection mechanism for sensing when the blunt portion of the Veress is in contact with the lung. For the emergency treatment of tension pneumothorax and/or hemothorax, it has the same disadvantages as described for Turkel.

Similar to Turkel and Steube, thoracentesis Veress-type needles with one or more automatic check valves are available commercially. These include the "Toramatic" devices (e.g. 1-55, 1-80, 1-VER) from Bioservice S.p.A. and Medax Medical Devices, "Safe-T-Centesis® Catheter Drainage System" from CareFusion, and the "Pleura-safe® Safety Thoracentesis Needle" from Allomed Medtech GmbH. However, for the emergency treatment of tension pneumothorax and/or hemothorax, these have the same disadvantages as already described for Turkel and Steube.

Regardless of use, the Veress needle assemblies of the art have not before been modified specifically for the emergent treatment of tension pneumothorax and/or hemothorax. Indeed, no Veress needle assemblies described have been used with a stable documenter to indicate a positive diagnosis for tension. Additionally, no method has to date been described for the safe treatment of tension pneumothorax and/or hemothorax using a device that simultaneously or near-simultaneously stably documents and treats the life-threatening process, with minimal risk to misdiagnosed patients. As such, there is a need for an emergency device and method to do so.

Each of the patents and published patent applications mentioned above are hereby incorporated by reference.

SUMMARY OF THE INVENTION

The present invention overcomes and substantially alleviates the deficiencies in the prior art by providing a method and device to simultaneously or near-simultaneously document and treat tension pneumothorax and/or hemothorax.

A primary object of the invention is to provide a method of simultaneous or near-simultaneous documentation and treatment of tension pneumothorax and/or hemothorax. Due to increased safety precautions that result in lessened risk to patients, this method provides an improved diagnostic and treatment means in high-risk patient populations.

Another object of the invention is to provide a method for empiric treatment based on at risk population characteristics, rather than solely depending on classic physical findings or delayed diagnostic means. This is possible with the use of the device described herein, which lessens the risks of injury to healthy lungs and documents the need (or lack thereof) for further follow-up treatment, such that in specific populations the potential benefits of rapid insertion outweigh the risks. For example, further research may identify soldiers in shock or sudden arrest wounded from penetrating thoracic trauma, patients with sudden cardiac arrest while being mechanically ventilated, patients undergoing cardiopulmonary resuscitation, and/or other groups as having benefit from immediate empiric insertion of device(s) to simultaneously or near-simultaneously document and treat possible tension pneumothorax and/or hemothorax, while risking only minimal chance of injury to healthy lungs if use is overly sensitive but less specific. As opposed to current common practice, this method may include bilateral use of said device(s).

Another object of the invention is to provide a method that is an improvement upon current art because it reliably documents successful treatment even for patients who have already been diagnosed with tension pneumothorax and/or hemothorax (e.g. by chest x-ray, ultrasound, computerized tomography, etc.). The documentation means allows for immediate confirmation of the successful treatment of tension buildup.

Another object of the present invention is to provide a device by which emergency personnel can rapidly document and treat tension pneumothorax and/or hemothorax, while introducing minimal risk of complications, such as lung or heart injury, open pneumothorax, and/or the need for unneeded further procedures. If employed on a patient who was misdiagnosed, the Veress-type needle reduces the chance of iatrogenic vital organ injury, check valve inhibits the introduction of iatrogenic pneumothorax, and pressure indicator documents the need for further procedures (e.g. thoracostomy).

Another object of the present invention is to provide a device for easily treating and documenting tension pneumothorax and/or hemothorax that can be used by out-of-hospital personnel with minimal experience and training, including under battlefield and mass casualty conditions.

Another object of the invention is to provide a sterile diagnosis and treatment device for the treatment of tension pneumothorax and/or hemothorax that can be efficiently packaged, stored, and carried into areas and situations that do not have access to standard diagnostic means (e.g. rapid x-ray or ultrasound).

Another object of the invention is to provide a device for documenting and treating tension pneumothorax and/or hemothorax that has a lumen which will not kink or be easily sealed during patient transport, thereby preventing occult tension pneumothorax.

Another object of the present invention is to provide a device for quickly and easily documenting and treating tension pneumothorax and/or hemothorax that can be used by in-hospital personnel, to provide for immediate diagnosis and stabilization until definitive treatment (e.g. thoracostomy) can be performed.

Another object of the present invention is to provide a disposable medical pressure gauge device which is simple and inexpensive in construction, efficient in operation, easy to manufacture and assemble, and that visually documents the current or past positive pressure within a cavity (e.g. the pleural cavity) of a patient.

Another object of the present invention is to provide a Veress-type needle assembly having a needle with a sharp end and a forwardly biased concentric probe with a blunt end, where the blunt end of the probe extends past the sharp end of the needle when no or minimal force is applied to the blunt end of the probe.

Another object of the invention is to provide a device that assists the user in determining and/or halting forward movement of a needle and/or probe upon penetration into a body cavity (i.e. pleural space).

Another object of the invention is to provide a device for documenting and treating tension pneumothorax and/or hemothorax that can be quickly and easily secured to a patient, so as to free the hands of medical personnel treating the condition and to prevent dislodgement.

Another object of the invention is to provide a device and method that can be used for the prevention and/or treatment of tension pneumothorax and/or hemothorax in high-risk patients, for example specific patients undergoing hyperbaric treatment, other changes in environmental pressure (e.g. helicopter transport, plane flight), or specific procedures (e.g. bronchoscopy or lung biopsy).

These and other objects of the invention are achieved by providing a tension pneumothorax and/or hemothorax treatment device having a Veress-type needle assembly, automatic check valve, and pressure indicator. In one embodiment, the Veress needle is composed of a longitudinally extending hollow needle which is sharp at its distal end to allow for puncturing the chest wall and extending into the pleural cavity, a longitudinally extending hollow probe which extends through the hollow needle and has a blunt distal end with one or more openings, a spring which is coupled to the probe and which resiliently biases the probe forward with respect to the hollow needle such that the blunt distal end of the probe extends past the sharp distal end of the needle, and a hollow housing which is fixed to the needle and which houses the spring and permits relative movement of the probe relative to the housing. The Veress needle section is fashioned such that it creates a path to an automatic check valve that permits flow of air and/or fluid only in a proximal direction. The connected Veress needle and automatic check valve are adapted to transmit the pressure of air and/or fluid within the pleural cavity to the interior surface of the pressure indicator, such that if a pressure greater than environmental (e.g. atmospheric) pressure is present, the pressure indicator will be urged proximally to lock in a proximal configuration. This allows the air and/or fluid to escape from the plural space through the device and into the external environment, thus immediately treating the tension pneumothorax and/or hemothorax. Additionally, this simultaneously, or near-simultaneously provides a stable indicator to be viewed by current and/or later medical personnel to positively document the diagnosis of current or previous increased pressure within the pleural cavity, thus indicating the likely need for further definitive treatment. If the pressure indicator does not move proximally, atmospheric pressure or less exists within the pleural cavity, thus indicating to current and later medical personnel the lack of a tension pneumothorax and/or hemothorax and the need to search for other causes for patient decomposition. The device can also include means for affixing the device to a patient and/or means for assisting the user in determining and/or halting forward movement upon penetration into a body cavity (i.e. pleural space). Thus, the provided assembly substantially reduces the possibility of iatrogenic lung puncture, automatically prevents the possibility of iatrogenic introduction of air into the pleural space, and allows for the simultaneous diagnosis and treatment of tension pneumothorax and/or hemothorax.

In one embodiment, the device may be inexpensively manufactured and is designed to be disposed of after one use. The Veress needle is preferably made of metal, such as stainless steel. The probe may be made of metal or plastic or other suitable material. The device housing and handle are made of rigid plastic. The device housing may be made of several parts which are joined together after the internal components are placed in the housing. The needle and/or catheter can be composed of a radio-opaque material and/or contain radio-opaque markers.

In one embodiment, the device also includes at least one means for securing the full device to a patient, such as by tape, glue, suture, or other means. A securing means can include a disk through which the needle projects that in practice is placed flush to the patient's skin. The disk can then be taped, sutured, stapled or otherwise adhered onto the patient. In another embodiment, the distal side (touching the patient's skin) of the disk is coated with a skin adhesive, so that the disk, and thus the full device, can be adhesively attached to the patient. Prior to use, the adhesive side of the disk is coated by a removable covering which does not affect the integrity of the adhesive when removed.

In one embodiment, there are different sizes of devices for different subgroups of patients (e.g. based on age, gender, weight, and/or length). These may come together in a kit, with means for determining proper sizing. For example, radiologic studies done by Harke et al. show mean chest wall thickness of deployed soldiers to be 5.36 cm, leading to a recommendation of 8 cm angiocatheter for needle decompression among adult males. It is advantageous to have differently sized devices for different subgroups, so long as the needle is of sufficient length to puncture the chest wall and extend into the pleural cavity, but not overly long to increase the risk of lung or heart injury. The appropriately sized device can be chosen for different subgroups based on weight, age, gender, length, pre-determined size categories (e.g. Broselow scale), and/or other indicators.

In one embodiment, the device includes one or more coupling mating means, such as luer or suction tubing coupling, which can be placed at the proximal end or near proximal end of the device. This allows the device to be reversibly hooked up to a syringe and/or suction system, so as to drain air and/or fluid through the device under negative pressure. This also may allow means to hook up the device to a three-way stopcock, which could alternatively be fully and irreversibly incorporated into the needle assembly.

In another embodiment of the present invention, the means for securing the device to the patient and/or the housing is adjustable, such that one device can be used on different patient groups (e.g. age, gender, weight, length, Broselow category). Under this embodiment, the device can be adjusted prior to (or alternatively during or after) insertion, such that the securing and/or housing means moves relative to the Veress-type needle to provide the desired exposed needle length for a specific patient (i.e. smaller exposed needle lengths for patients with smaller chest wall thicknesses; larger for patients with larger chest wall thicknesses). By way of example, this could be done via a sliding gripping stopper, twisting screw, tabs and notches, or other mechanism. The device can contain a means for setting this length based upon one or more pre-determined patient groups (e.g. age, gender, weight, length, Broselow category), which are indicated on the device. The needle may additionally have distance (e.g. centimeter) markings along its external length for easy measurement of depth.

In yet another embodiment of the present invention, the automatic check valve and pressure indicator mechanisms are fully and/or partially combined, so as to minimize parts and/or manufacturing cost. Under this embodiment, the device is formed such that the initial opening of the automatic check valve serves to provide stable documentary evidence of previous or current increased pressure within the pleural cavity, thus indicating the likely need for further definitive treatment while allowing air and/or fluid to immediately escape from the pleural space through the device and into the external environment.

In yet another embodiment, the Veress-needle assembly provides visual and/or audible signals to a practitioner when the pleural cavity has been reached and/or indicates to the user if the blunt tip distal end of the inner needle has made contact with the lung. This mechanism may be standard (using one spring) or more sensitive (using two or more), in manners similarly disclosed in U.S. Pat. No. 5,334,159 to Turkel and/or U.S. Pat. No. 6,447,483 to Steube et al which are hereby incorporated by reference herein.

In yet another embodiment, the device includes a means for automatically halting the forward movement of the device upon penetration into a body cavity (e.g. pleural space). In one embodiment of this mechanism, the external movement of the Veress-probe in relation to the needle tip during use causes movement of the probe within the housing such that an external stabilizer that is flush with the patients skin can move in relation to the rest of the device only when the probe tip is in the proximal position in relation to the needle tip (e.g. penetrating chest wall) and will not move when the probe is in the extended distal position (e.g. in the pleural cavity). This mechanism automatically prevents the user from penetrating the device too far into the body cavity and thus injuring vital organs or other structures.

In yet another embodiment, the device includes a catheter (which can include a check valve) over the Veress-needle that can remain within the patient, if the pressure documenter indicates that there is or was tension, which may be in a manner similarly disclosed in U.S. Pat. No. 7,229,433 to Mullen which is hereby incorporated by reference herein. In this embodiment, there is the option of a second step where the rest of the device is removed from the patient leaving the catheter within the chest cavity.

In yet another embodiment, the device comprises initially separate stabilization means, Veress-type needle device, and pressure documenter means that can be reversibly combined. In different embodiments, both or either of the Veress needle and pressure documenter have an automatic check valve. These sections can be combined into one device prior to use on a patient.

In yet another embodiment, other means for the indication of pressure are employed to stably document the presence of tension (increased pressure) before, during, or shortly after its release. For example, under one embodiment the pressure indicator is a liquid column (e.g. sterile water, normal saline, or other suitable liquid). Such liquid may be colored (e.g. with green dye) such that is easily visible or other means for more easily viewing the liquid may be employed (e.g. shiny metallic flakes). When tension is present, pressure forces the liquid out of the device or into another chamber such as to indicate stably the diagnosis. Under various embodiments the pressure indicator is another type of piston mechanisms (e.g. movable ball valve); a burst disk; a bourdon or other aneroid type gauge; a folded or otherwise coiled tube or balloon, such that pressure causes uncoiling and/or release; an electronic sensor (e.g. a piezoresistive strain, capacitive, electromagnetic, piezoelectric, optical, potentiometric, resonant, thermal, or ionizing sensor); an optical or other type of sensor that directly senses the opening of the check valve; or any other type of force collector (e.g. diaphragm, piston, bourdon tube, bellows) that measures strain or deflection due to applied force over an area.

In yet another embodiment, the device and method includes a means for measuring and/or viewing negative pressure, in addition to stably documenting increased pressure (i.e. tension). Under this embodiment, the pressure documenter portion of the device can show negative pressure, indicating that the device has entered a healthy pleural space without tension in a patient breathing spontaneously. This may be achieved via any of the aforementioned means for sensing pressure, other mechanical means, or via electronic means in a manner similarly disclosed in U.S. Pat. No. 5,421,821 to Janicki et al that is hereby incorporated by reference herein.

In yet another embodiment, the device includes a means for protecting the user from a needle stick injury when removing the device from the patient. Under this embodiment, such means can be arranged from any one of the many self-blunting needle mechanisms for intravenous catheters or phlebotomy needles that are well known in the art. This mechanism may involve the locking of the probe in its distally extended "blunt" configuration.

In yet another embodiment, the method includes the insertion(s) of the device of the present invention prior to the development of tension pneumothorax and/or hemothorax, to prevent and document the dangerous development of tension. Under this embodiment, identified high-risk patients would have the device inserted unilaterally or bilaterally prior to high-risk activities, such as hyperbaric treatment, other changes in environmental pressure (e.g. helicopter transport, plane flight), or specific procedures (e.g. bronchoscopy and/or lung biopsy).

There have been illustrated and described herein methods and devices to simultaneously or near-simultaneously document and treat tension pneumothorax and/or hemothorax. While particular embodiments of the invention have been described, it is not intended that the invention be limited thereto, as it is intended that the invention be as broad in scope as the art will allow and that the specification be read likewise.

From the foregoing, it can be seen that the present invention provides an effective means for treating tension pneumothorax and/or hemothorax within animals, especially humans. Moreover, it should also be apparent that the device can be made in varying lengths and sizes to treat adults, children, and infants. While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification and that elements of certain embodiments can be combined with elements of other embodiments. Additional objects, advantages, and novel features of the invention will be set forth in the description which follows, and will become apparent to those skilled in the art upon examination of the following detailed description and figures. It should be understood that not all of the features described need be incorporated into a given method or device.

DETAILED DESCRIPTION OF THE INVENTION

Figure 1:
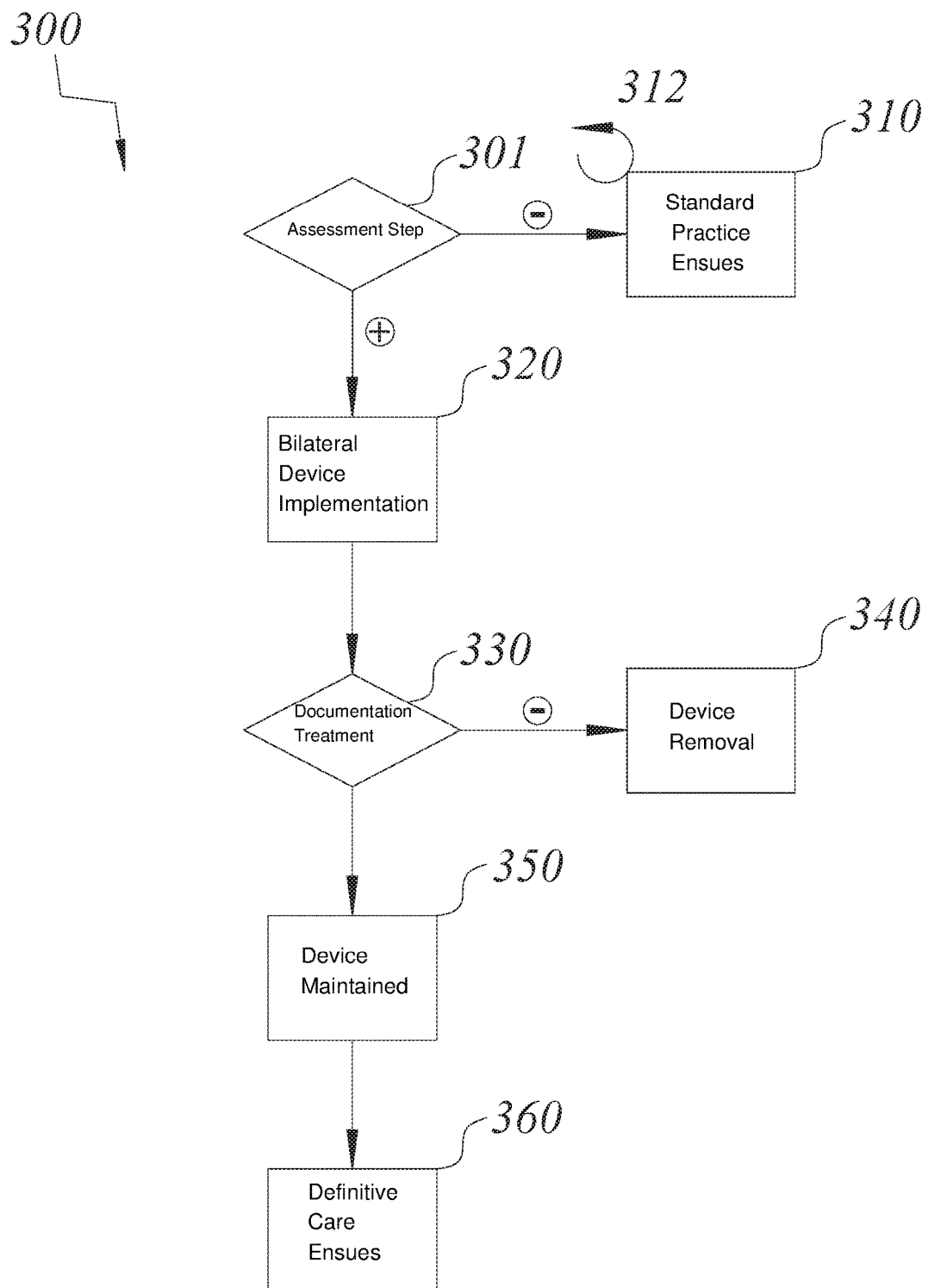
FIG. 1 is a block diagram of the method according to an embodiment of the invention for the simultaneous or near-simultaneous documentation and treatment of tension pneumothorax and/or hemothorax.

Referring to the drawings, FIG. 1 generally shows the one embodiment of a method and workflow 300 for the treatment of tension pneumothorax and/or hemothorax. This method and workflow of the present invention 300 should be assumed to fit within standard emergency care protocol well known in the art (and not described here), which may also be assumed to be occurring previous, after, and potentially parallel throughout, especially when there is more than one practitioner caring for a particular patient. Additionally, methods of standard needle use, patient cleaning, equipment disposal, and other standard medical practice well known in the art are not described here.

First, an out-of-hospital or in-hospital practitioner performs a rapid and low-cost assessment to decide if a patient meets pre-determined risk group criteria at step 301. As aforementioned, these risk group criteria can be a combination of signs, symptoms, and/or risk factors and are not described in detail here.

If the result of the assessment 301 is negative, there is no deployment of the intervention and standard practice ensues at step 310 (not explained in detail here). The patient may continue to repeatedly be assessed for risk group criteria as shown by loop 312 and, if the patient's condition evolves to meet such criteria the workflow restarts at assessment point 301.

If the assessment result 301 is positive for meeting risk group criteria, bilateral implementation of device(s) ensues at step 320. This is followed by the simultaneous or near-simultaneous documentation and treatment of tension pneumothorax and/or hemothorax at step 330 if present in the patient. This may be performed with two devices or, alternatively, with one device used on both sides in cases where the first side is negative for tension and device cost is a significant concern.

If step 330 does not document tension, then the device is removed at step 340 either by the primary user or by a later higher level of care (e.g. after transport or the arrival of more qualified medical personnel). If device removal 340 is not to be immediate, the device can be secured to the patient to prevent inadvertent removal and/or movement.

If step 330 does document tension, then the device is maintained at step 350. The device may be secured to the patient at this time to prevent inadvertent removal and/or movement. Standard care can then be resumed or focused on, as it may have been occurring parallel throughout the method and workflow 300 of the present invention.

After step 350, definitive care next ensues at 360 on the side(s) documented as positive for tension. Definitive care 360 is most frequently a tube thoracostomy, but encompasses any type of definitive care for tension pneumothorax and/or hemothorax (e.g. thoracotomy). It should be noted that longer-term maintenance and/or monitoring of the inserted device of the current invention may be sufficient for definitive care 360 (e.g. hooking up the device to suction). Definitive care 360 may be performed by the primary user or by a later higher level of care (e.g. after transport or the arrival of more qualified personnel). Standard care (not described here) then continues.

Figure 2:
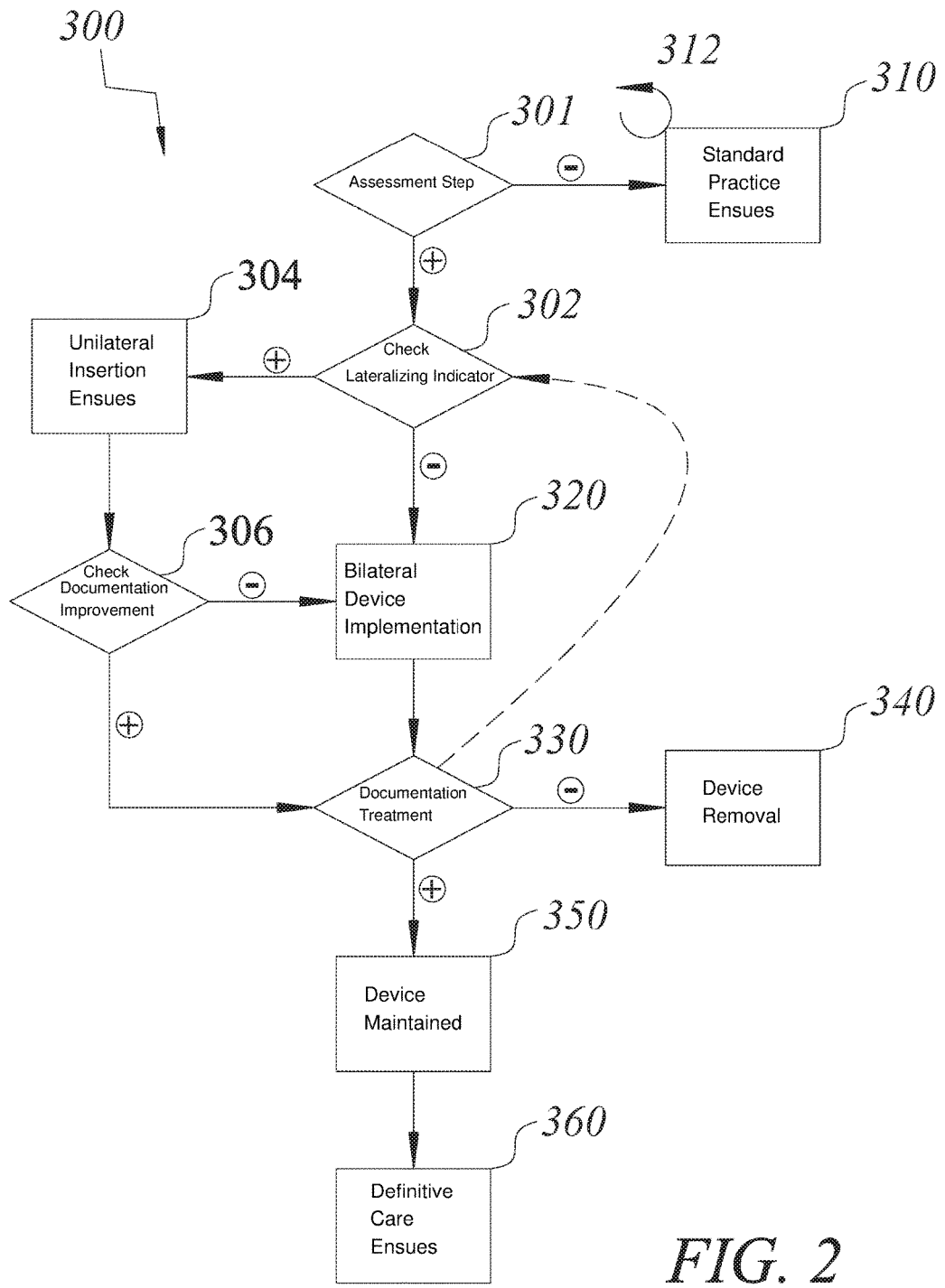
FIG. 2 is a block diagram of the method according to an embodiment of the invention for the simultaneous or near-simultaneous documentation and treatment of tension pneumothorax and/or hemothorax.

FIG. 2 generally shows another embodiment of the method and workflow 300 for the treatment of tension pneumothorax and/or hemothorax under the present invention. In this embodiment, after assessment step 301, there is inserted a step for checking for lateralizing indicator(s) 302. This may be performed by auscultation, ultrasound, or other rapid means that help identify the side of the possible tension pneumothorax and/or hemothorax, if such is present only on one side.

A practitioner may enter the workflow at step 302 when there is a positive documentation of tension under step 330 after the placement of the first device (in what was going to be bilateral placement, but before the placement of the second device). A practitioner may enter the workflow at step 302 having already confirmed, via standard diagnostic means (e.g. chest x-ray, computed tomography, ultrasound, or other means), the presence of a unilateral or bilateral tension pneumothorax and/or hemothorax.

If such lateralizing indicator(s) 302 are not present, bilateral insertion of device(s) ensues at step 320, along with the further steps as previously outlined. This also occurs in the case of confirmed bilateral tension pneumothorax and/or hemothorax.

If such lateralizing symptoms 302 are present, unilateral insertion ensues at step 304, in such side as presumed to have the tension pneumothorax and/or hemothorax. Next, a check for positive documentation and clinical improvement is done at step 306. If the patient did not have documented tension on that side or has not improved, then a device is placed on the other side for bilateral device implementation 320 (except in cases where this has already been definitively ruled out). If the patient had documented tension and improved with unilateral placement, then no additional device is placed on the other side. Regardless, both paths result in the simultaneous documentation and treatment of tension pneumothorax and/or hemothorax if present 330 on the side(s) inserted. The further steps as previously outlined then ensue.

Figure 3:
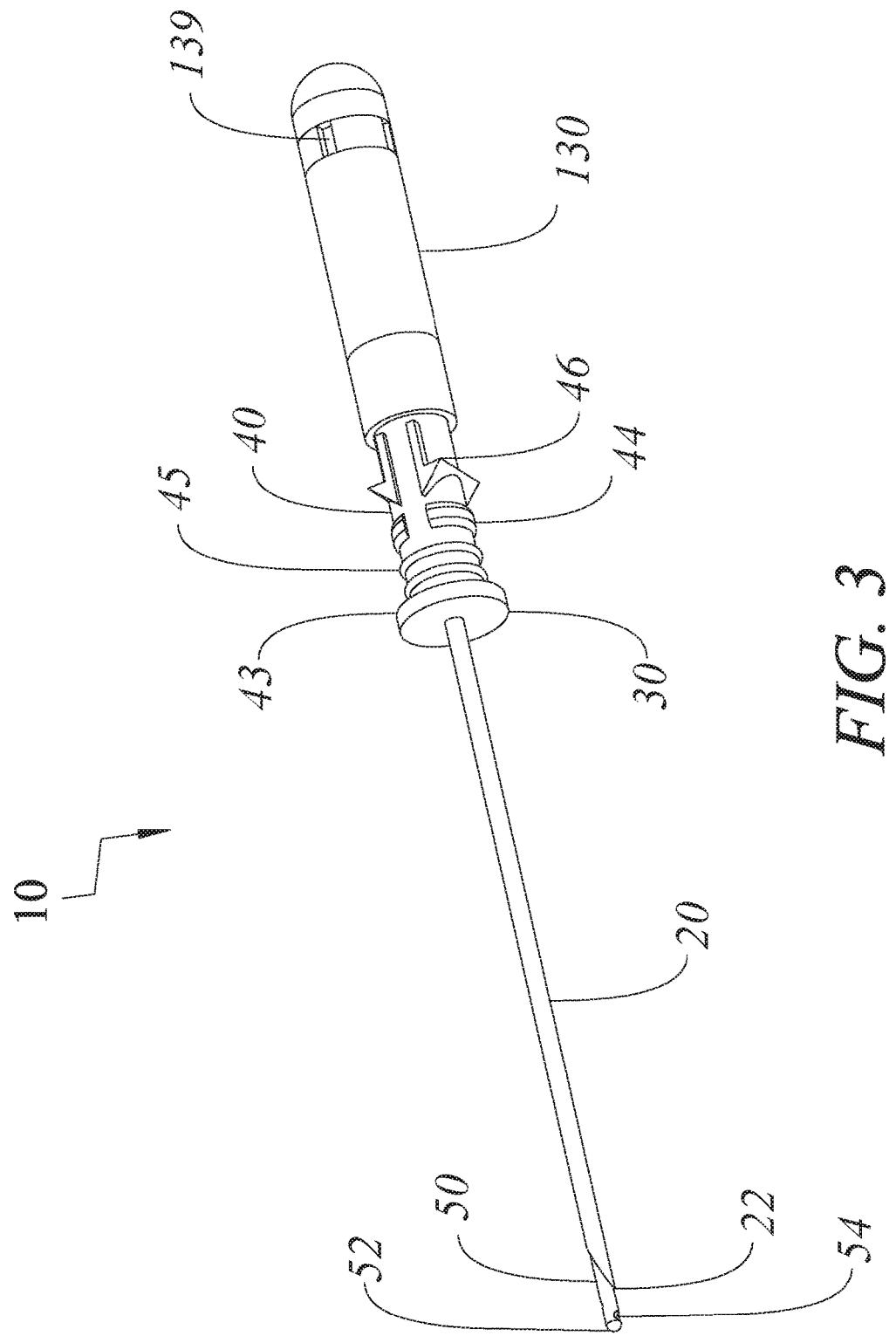
FIG. 3 is a perspective view of a tension treatment device of the present invention in accordance with one embodiment, as assembled prior to use.
Figure 4:
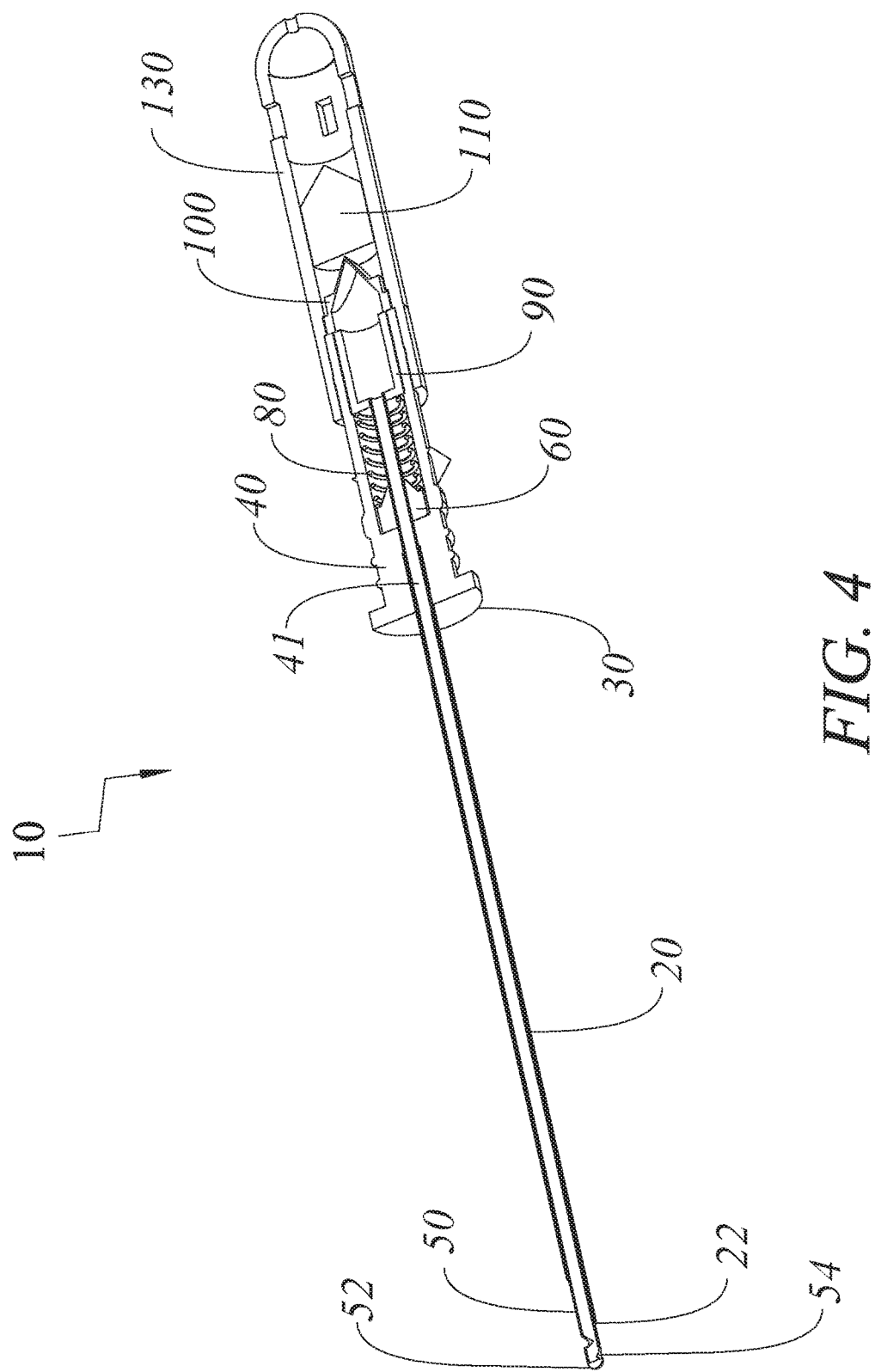
FIG. 4 is a cross section view of a tension treatment device of the present invention in accordance with one embodiment, as assembled prior to use.

Moving now to FIGS. 3 and 4, one embodiment of a device of the present invention device is illustrated and generally indicated as 10. For ease of reference, distal shall refer to the end of the device farthest away from the user, while proximal shall refer to the end of the device closest to the user.

The device generally comprises a needle assembly 10 made up of several parts, including: a longitudinally extending hollow needle 20, a stabilization device 30, a hollow housing 40, a hollow probe 50, a probe holder 60, a spring 80, a cylinder 90, an automatic check valve 100, a tension documenter 110 and a mating cap 130. Together, the needle 20, housing 40, probe 50, and spring 80 can function as a Veress-type needle assembly.

Figure 5:
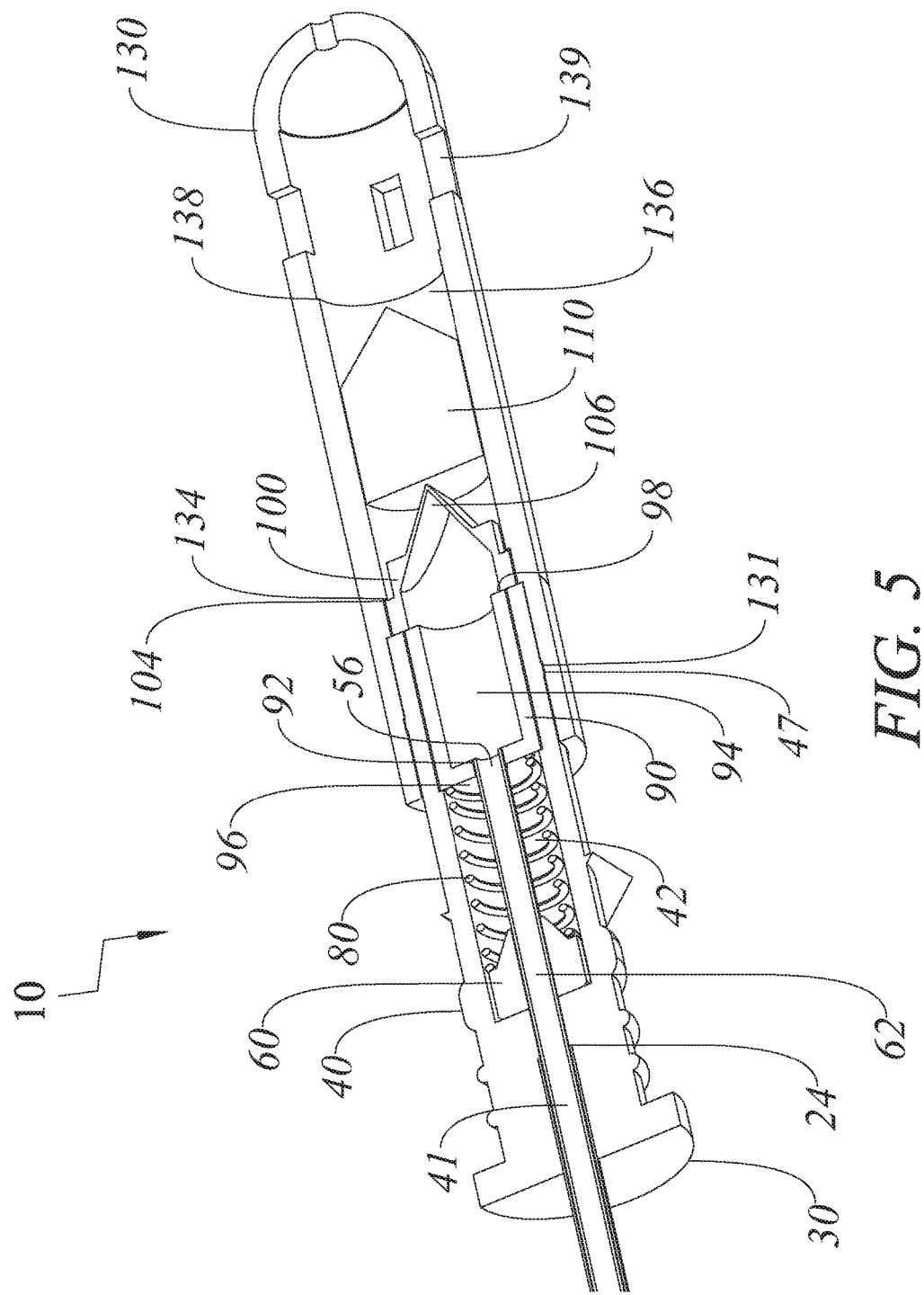
FIG. 5 is a detailed cross section view of the proximal components of a tension treatment device of the present invention in accordance with one embodiment, as assembled prior to use.
Figure 6:
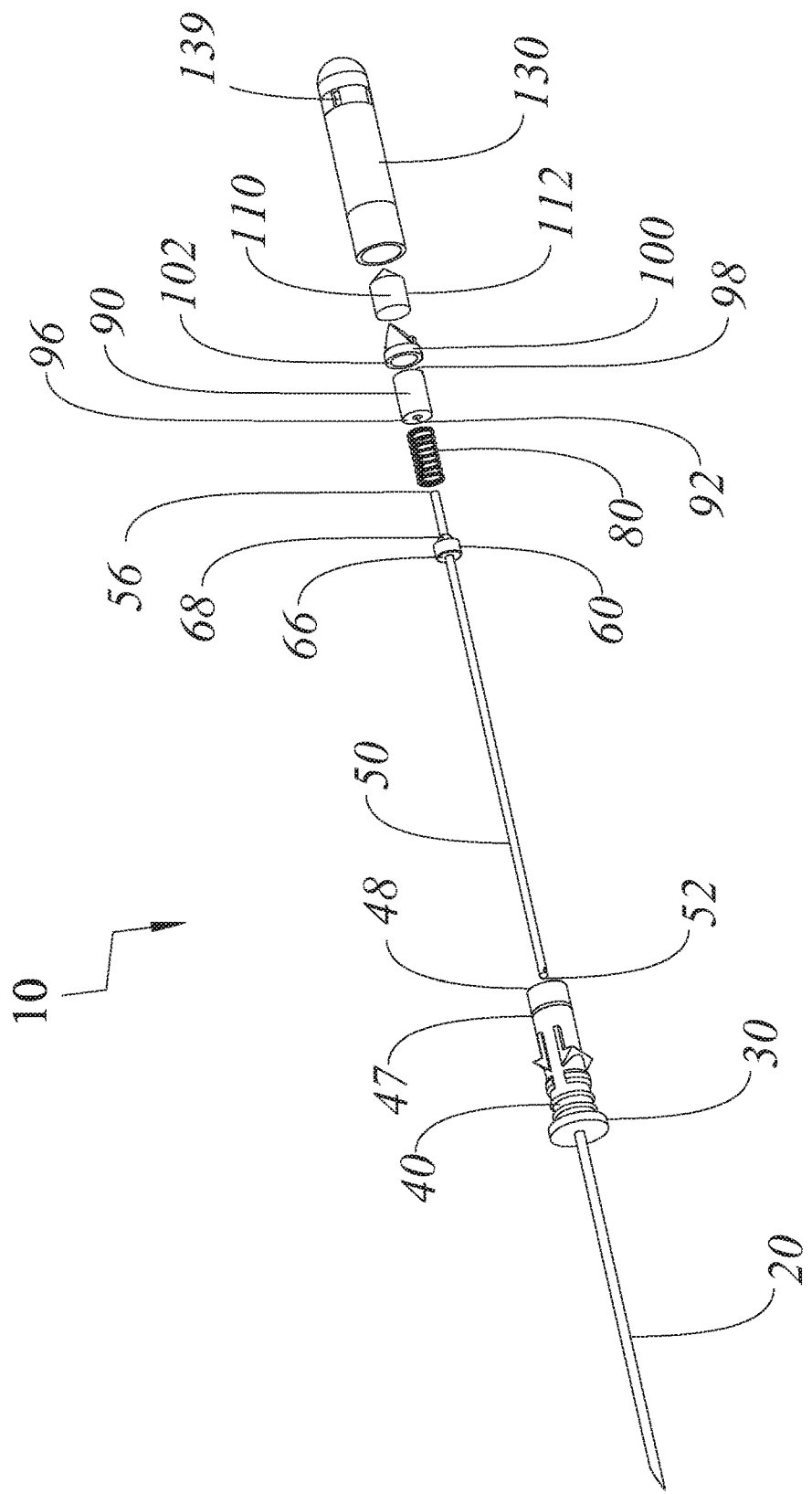
FIG. 6 is an expanded perspective view of a tension treatment device of the present invention in accordance with one embodiment, shown in an expanded view before assembly.

Turning to FIGS. 5 and 6 in conjunction with FIGS. 3 and 4, it is seen that hollow needle 20 has a sharp distal end 22 and a proximal end 24. Hollow needle 20 is preferably molded into housing 40 such that the proximal end 24 of the needle is securely held in housing 40. Thus, housing 40 is provided with a passage 41 in which the needle is held. The needle 20 additionally passes through stabilizer 30.

Passage 41 opens up into an open interior of housing 40 that can include a cylindrical chamber 42 which is sized to receive other internal components as discussed herein after. The outer surface of housing 40 is preferably provided with abutment 43, ribs 45, and visual indicators 44 and 46, as well as a proximal portion with grooves 47 and abutment surface 48. Ribs 45 are provided as finger grips, while abutment 43 prevents the practitioner's hand from sliding off of housing 40. Proximal grooved portion 47 and abutment surface 48 provide a mating surface for the distal portion of mating cap 130. Housing 40 may be sufficiently transparent and have external visual indicators 44 and 46 that can be used respectively as reference points to indicate when probe holder 60 (viewed within chamber 42) is in its distal or proximal position and thus when connected probe 50 is extended or retracted.

The hollow probe 50 may be a standard Veress-type needle probe having a blunt distal end 52 with one or more ports or openings 54, and a proximal end 56. The opening(s) 54 in distal end 52 are provided to permit air and/or fluid to enter a generally hollow interior of probe 50 from the body cavity entered (e.g., the pleural cavity). Probe 50 (with probe holder 60 as discussed following) is inserted into chamber 42 and extends out through needle 20, such that (as seen in FIGS. 3 and 4) the blunt distal end 52 of probe 50 extends past the sharp distal end 22 of the needle 20. Proximal end 56 of probe 50 extends through spring 80 and into orifice 92 of cylinder 90.

Probe holder 60 is can be plastic or metal and colored or otherwise marked to make it easier for viewing within housing 40. It has an axial passage 62 through which probe 50 extends axially in both directions. Holder 60 can be melded to probe 50 to hold it securely without movement between the two parts. Chamber 42 of housing 40 receives probe holder 60, along with probe 50 (as previously mentioned). Probe holder 60 can be fashioned such that its distal cylindrical segment 66 fits into cylinder 42 of housing 40 (i.e., the outer diameter of holder 60 is just slightly smaller than the inner diameter of chamber 42). The proximal end of holder 60 is preferably a frusto-conical segment 68 in shape, which fits inside spring 80, thus providing a seat and centering mechanism.

Spring 80 provides a biasing mechanism or means for biasing for probe 50 as transmitted through probe holder 60, with the distal end of spring 80 resting on probe holder segment 68. The proximal end of spring 80 abuts distal cylinder surface 96, with the proximal end 56 of probe 50 extending through spring 80. While spring 80 is preferably a spring as is commonly known in the art, it should be appreciated that other resilient biasing mechanisms could be otherwise utilized (e.g. a piece of elastic or rubber with a hole for fluid communication).

Cylinder 90 can be formed of plastic and be a substantially hollow cylinder, including an opening 92 in its distal end through which the proximal end 56 of hollow probe 50 terminates within chamber 94; the diameter of opening 92 is preferably just slightly larger than the outer diameter of proximal probe end 56, which can form an air-tight seal. Cylinder 90 also has distal end 96 which provides a housing and stop for spring 80. Spring 80 is thus held between the proximal segment 68 of probe holder 60 and the distal end 96 of cylinder 90, thereby effectively acting to bias probe 50 in a distal position relative to needle 20. Additionally, cylinder 90 has ledge 98 which provides a stop and connection mechanism for automatic check valve 100, such as to provide an air-tight seal between check valve 100 and ledge 98. Thus, preferably no air is permitted to enter probe 50 to move in the distal direction due to check valve 100 and seal(s) between proximal end 56, ledge 98, cylinder 90, housing 40, cap 130, and/or additional sealing means (e.g. O-ring(s)), depending on different embodiments. However, air and/or fluid may move proximally from within the hollow probe end 56 and out of chamber 94 through automatic check valve 100 and into mating cap 130. Check valve 100 is therefore one example of a means for permitting fluid to flow proximally through the device while preventing fluid from flowing distally through the device.

In one embodiment, automatic check valve 100 is a duck billed valve. However, it should be appreciated that numerous different types of automatic check valves could be utilized by those of standard knowledge of the art. Valve 100 has a distal ring surface 102 which, as previously mentioned, mates to form an air-tight seal with ledge 98 of cylinder 90. Air and/or fluid is able to move only in a proximal direction through the center of the valve 106. Check valve 100 also has a proximal ring surface 104 upon which the distal surface 134 of mating cap 130 rests to minimize movement of valve 100 and assist in providing seal.

A pressure indicator such as tension documenter 110 can be made of plastic with the color being red or another easily visible color. Tension documenter 110 fits within cap 130 such that the outer diameter of documenter 110 is just slightly smaller than the inner diameter of chamber 136, allowing documenter 110 to slide proximally within chamber 136 in order to function as a means for providing a stable visual indication of whether air has passed proximally through the device. Although ridge(s) 138 can allow documenter 110 to move in a proximal direction, they can also prevent its movement in a distal direction once it has passed proximally. Mating cap 130 generally comprises a hollow cylinder made of, for example, plastic, of which at least the proximal portion is transparent and/or has holes 139 to allow visualization of documenter 110 when in its proximal position. The distal inner surface of mating cap 130 includes grooves 131 to match up with ridges 47, so that cap 130 can mate with housing 40 (which is connected to needle 20 and stabilizer 30) to secure the rest of the contents of device 10 within. Cap 130 can be fixed to housing 40 by glue, sonic welding, or other means well known in the art. Finally, cap 130 includes opening(s) 139 to provide an exit for air and/or fluid into the external environment. These holes may be covered to minimize possible splashing of fluid into the eyes of the user. In other embodiments, cap 130 has a luer lock or other syringe fittings, ports, or connections to suction and/or drainage tubing that can serve as the exit for air and/or fluid into the external environment and/or provide the ability to hook up device 10 to a syringe and/or suction. In such embodiments, device 10 may also include a sealing cap that reversibly connects to the connector(s).

Figure 7:
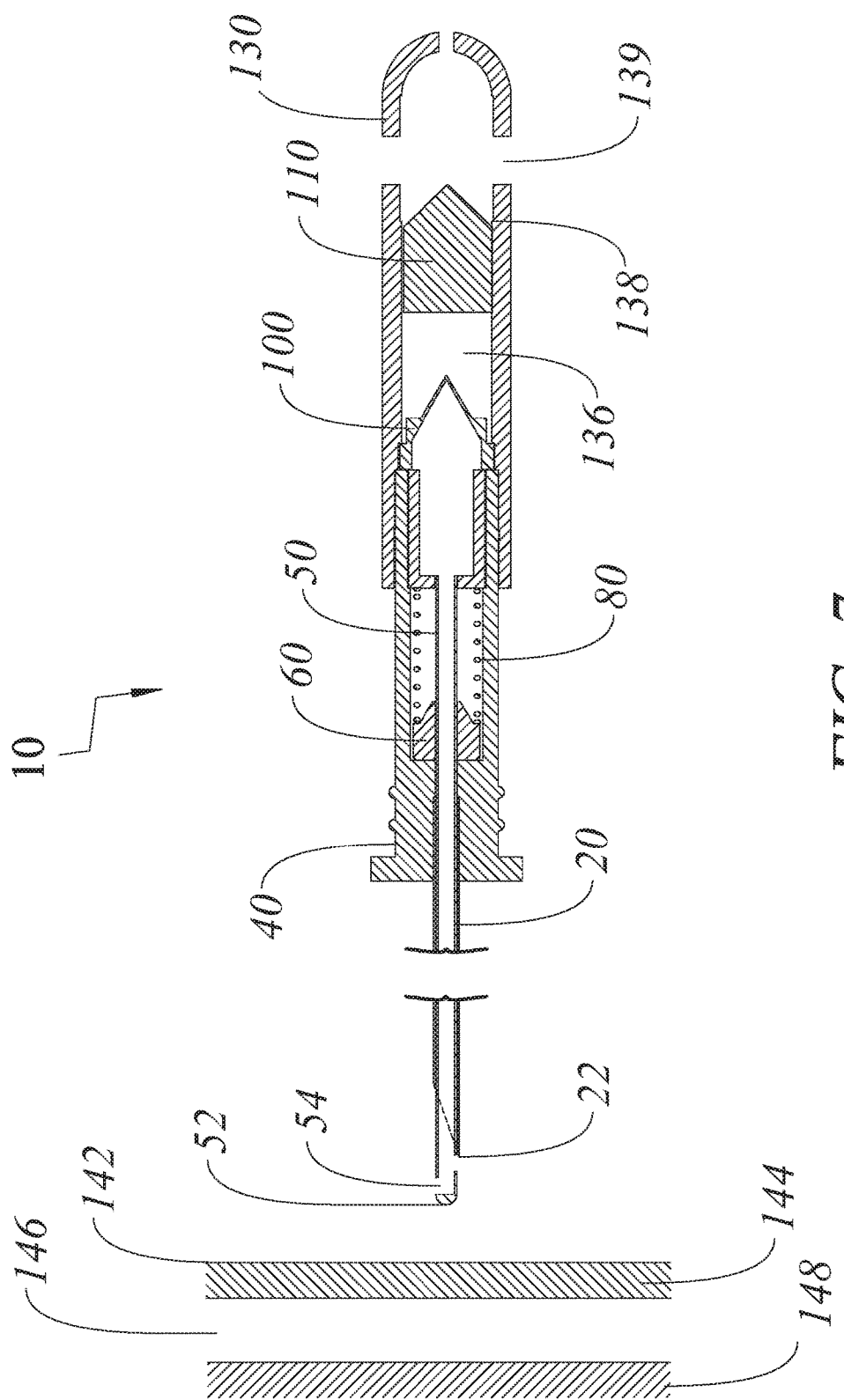
FIG. 7 is a cross-sectional side view of a tension treatment device of the present invention in accordance with one embodiment, shown as assembled prior to insertion into the chest cavity.

Moving now to FIGS. 7-11, needle assembly 10 of an embodiment of the invention is described in use. In FIG. 7, the assembly 10 is shown before insertion into the example of a human body with skin 142 covering a chest wall 144 within which lies a pleural cavity 146 and lung 148. Probe holder 60 is in its distal position and tip 52 of probe 50 extends out distally from the tip 22 of needle 20, due to the biasing action from spring 80 on probe holder 60 and thus probe 50 as previously described. Additionally, tension documenter 110 within chamber 136 of mating cap 130 is in its initial distal position, preferably lightly held there by slight tension with the walls of cavity 136; ridges 138; lubricant, liquid, or jelly; and/or other such means. Thus, the user cannot see the colored documenter 110 through holes 139 and within cavity 136, which alerts the user to the device being ready to use.

Figure 8:
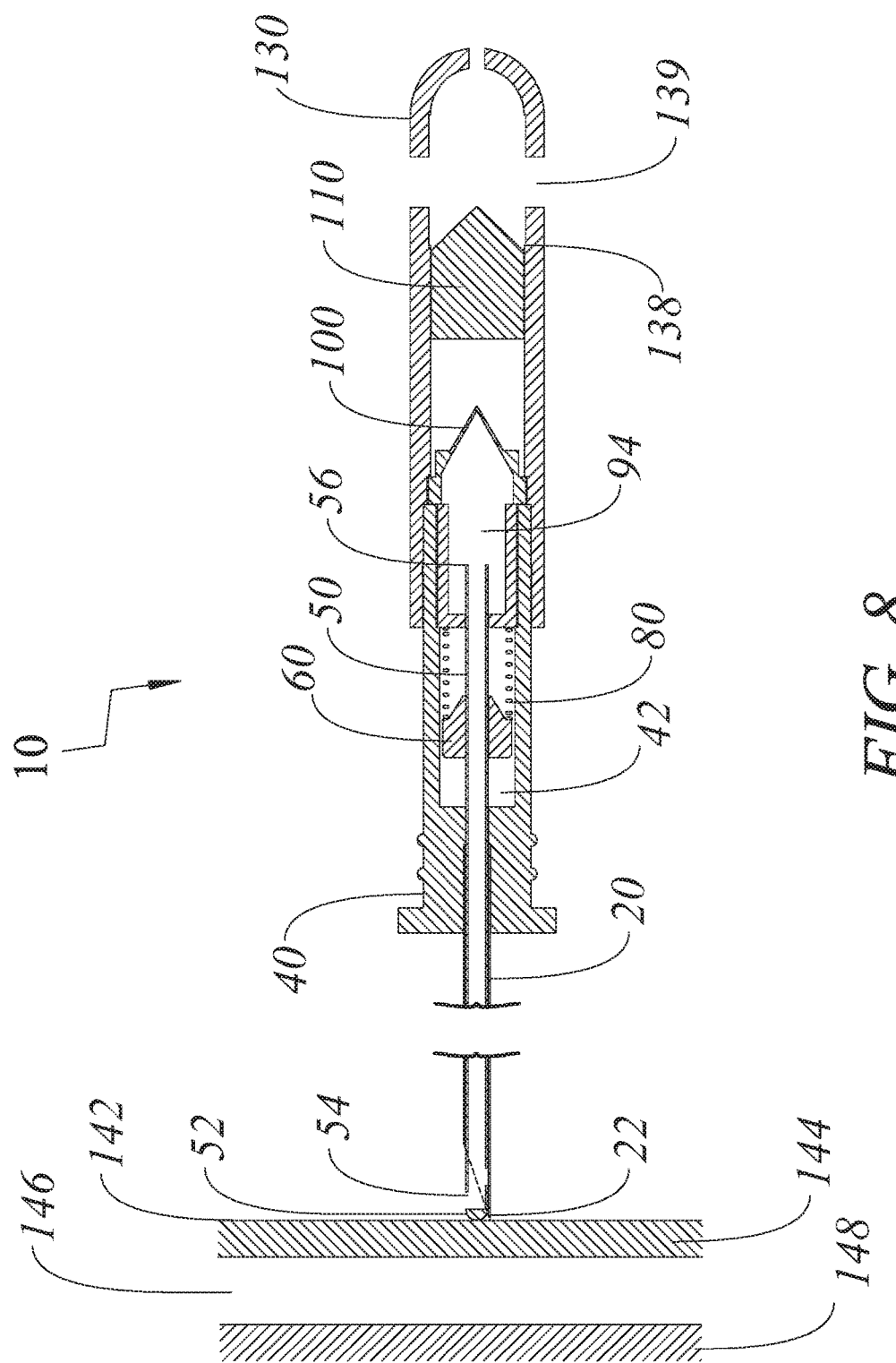
FIG. 8 is a cross-sectional side view of the tension treatment device of FIG. 7, shown upon contact with the skin.

FIG. 8 demonstrates when probe end 52 first touches the skin 142. This causes probe tip 52 to move proximally in reference to needle tip 22, and likewise probe 50 to move proximally in reference to needle 20 and housing 40. As probe 50 is adhered to probe holder 60, this causes holder 60 to start to move proximally within cavity 42, thus compressing spring 80. Additionally, proximal probe end 56 starts to move within chamber 94.

Figure 9:
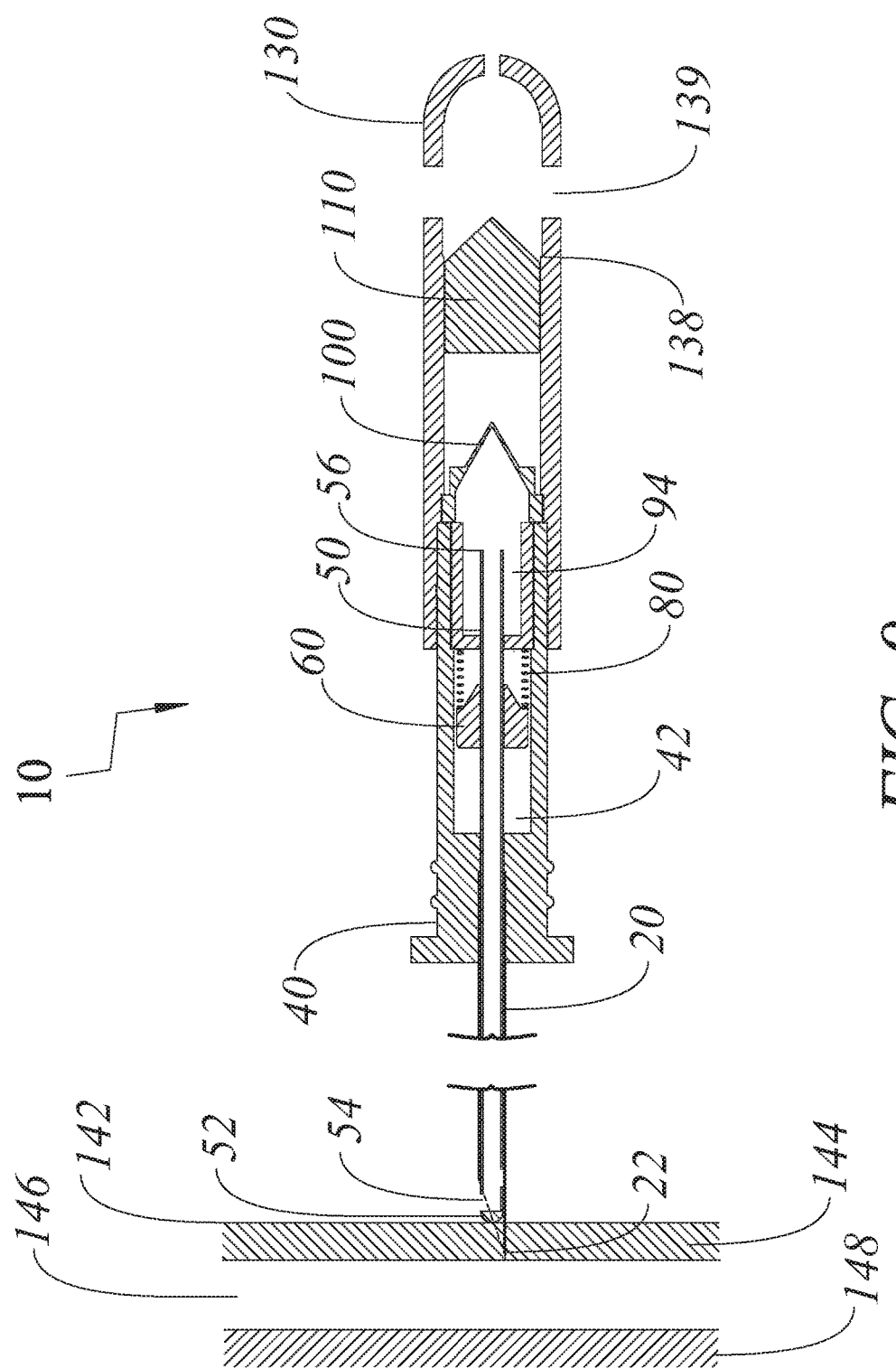
FIG. 9 is a cross-sectional side view of the tension treatment device of FIG. 7, shown upon first penetration of the chest wall.

Moving now to FIG. 9, when needle 20 pierces skin 142 and starts to enter chest wall 144, it causes probe tip 52 to move further proximally in reference to needle tip 22. Likewise, probe 50 moves further proximally in reference to housing 40, holder 60 moves further proximally within cavity 42, and proximal probe end 56 moves further proximally within chamber 94.

Figure 10:
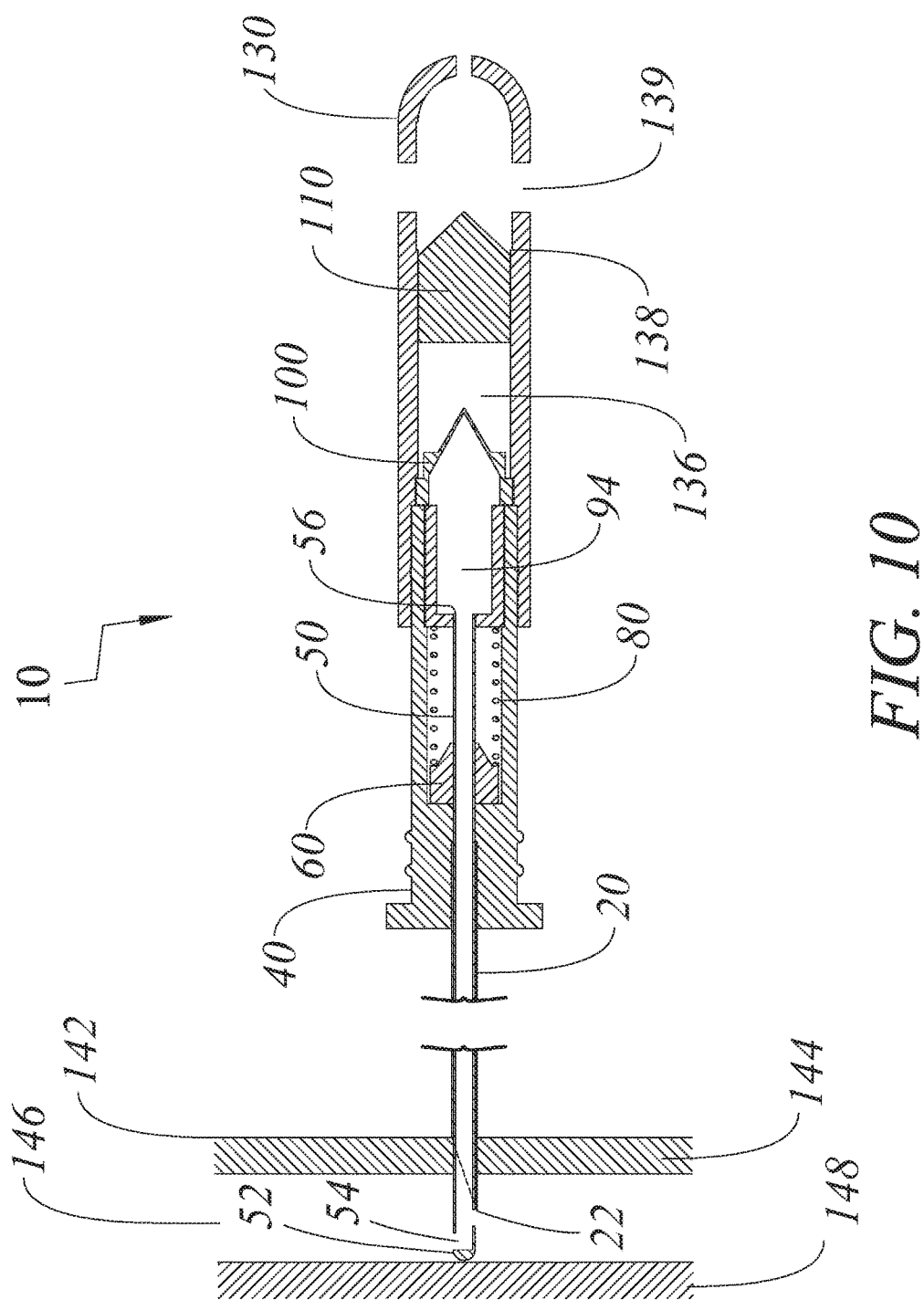
FIG. 10 is a cross-sectional side view of the tension treatment device of FIG. 7, shown upon entrance into the pleural space when there was no tension present.

FIG. 10 demonstrates device 10 used with a patient without a tension pneumothorax and/or hemothorax, who thus has a lower pressure in the pleural space 146 compared to the external environment outside opening 139. Once needle 20 pierces chest wall 144 and enters pleural space 146, spring 80 acting upon holder 60 forces probe 50 to move distally in reference to housing 40 and needle 20, thus projecting probe tip 52 distal to needle tip 22 and exposing probe opening(s) 54 within pleural space 146. Therefore, the extended blunt probe end 52 serves to protect lung 148 (or other vital structures) from the sharp distal needle tip 22, providing one of the benefits of the current invention.

As probe opening(s) 54 are then exposed to pleural space 146, they connect the pleural space 146 to the proximal probe opening 56 through hollow probe 50, forming one continuously open connected space. However, as long as the pressure in pleural space 146 is equal to or less than that of the external environment outside opening 139, check valve 100 prevents air from entering chamber 94 and thus probe end 56, preventing the introduction of air (i.e. an iatrogenic open pneumothorax) to the patient. Additionally, if as in FIG. 10 there is no tension pneumothorax and/or hemothorax in the pleural space 146 and thus lower pressure in the pleural space 146 compared to the external environment outside opening 139, there is no cause for movement of tension documenter 110. Thus, after insertion through the chest wall 144, the user can still not see the colored documenter 110 within cavity 136 through hole 139, which alerts current and later medical personnel that the patient did not have a tension pneumothorax and/or hemothorax on that lung side.

Figure 11:
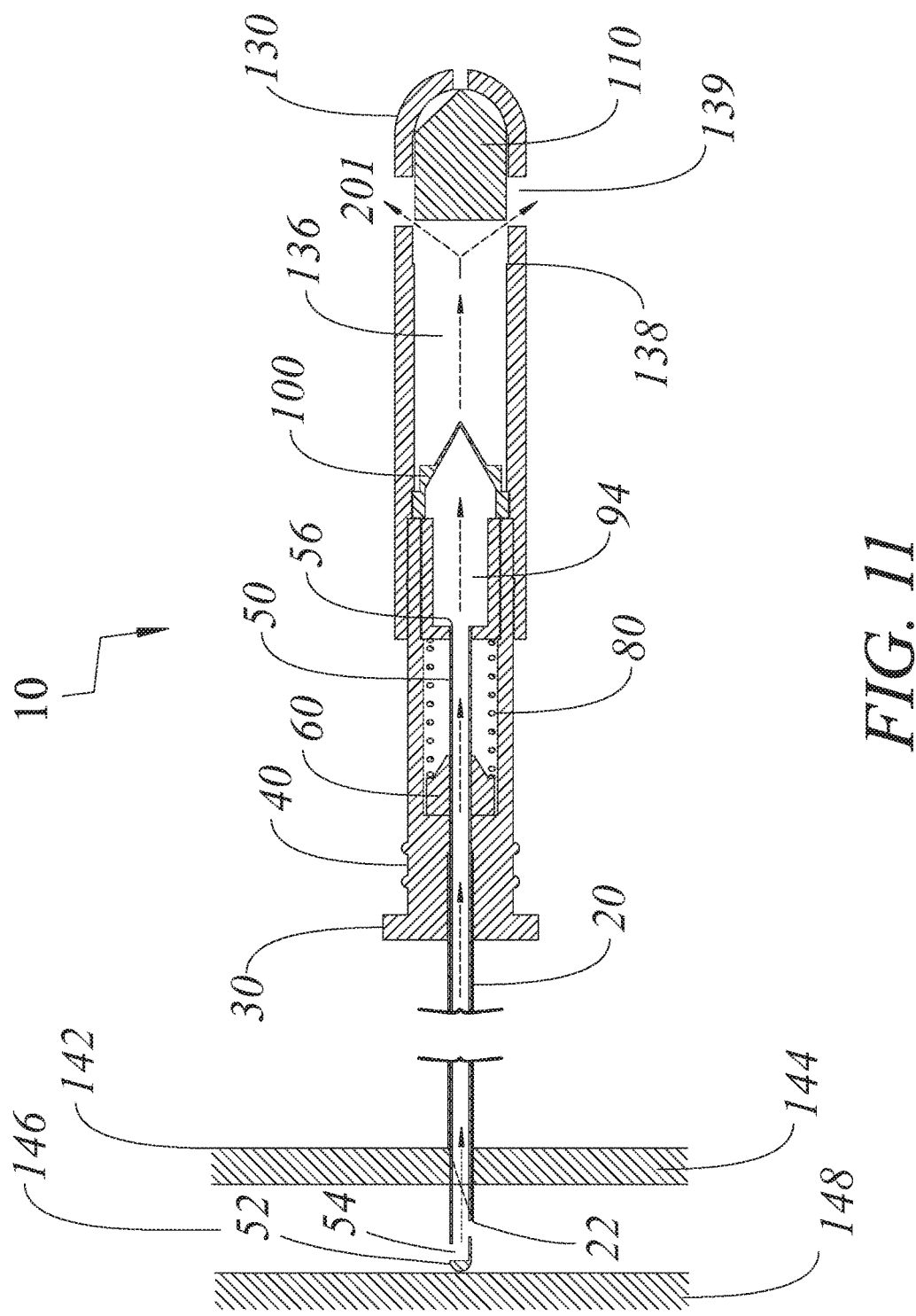
FIG. 11 is a cross-sectional side view of the tension treatment device of FIG. 7, shown upon entrance into the pleural space when there was tension present.

FIG. 11 demonstrates device 10 used with a patient who has a tension pneumothorax and/or hemothorax, and thus has a higher pressure in the pleural space 146 compared to the external environment outside opening 139. As shown by arrows 201, this increase pressure in pleural space 146 is transmitted through probe opening 54 and flows through hollow probe 50 to proximal probe opening 56 and into chamber 94. From there, the rush of air and/or fluid passes through valve 100, as it is a higher pressure than the external environment, and into chamber 136. Within chamber 136, the pressure propels mobile documenter 110 proximally, relative to cap 130, where it becomes locked proximally by ridges 138. This allows air and/or fluid that was trapped within the pleural space 146 to exit via hole(s) 139 and into the external environment, thus relieving the dangerous tension within the body. Check valve 100 prevents any air from moving back distally. Additionally, colored documenter 110 is now viewable through hole(s) 139 and within the (preferably transparent) proximal portion of cavity 136, which alerts current and later medical personnel that the patient had a tension pneumothorax and/or hemothorax on that lung side and thus likely requires additional definitive care (e.g. tube thoracostomy).

The full device 10 may then be secured (not shown) to the patient and stabilized using stabilizer 30. In one embodiment, this is done by further inserting needle 20 until stabilizer 30 is flush with patient's skin 142. Then, as by one of the many common means of adhering devices to patient skin known in the art (e.g. tape, glue, suture, staples, etc.), with or without adhesive previously applied to stabilizer 30 that can then be exposed, the device is secured to the patient. As aforementioned, in another embodiment of the present invention, stabilizing device 30 and/or housing 40 can be adjustable, such as to alter the full exposed length of the needle 20. This could either be done after insertion and once through the chest wall 144, moving the stabilizer 30 to become flush with patient's skin 142, or prior to insertion based on predicted chest wall thickness.

Figure 12:
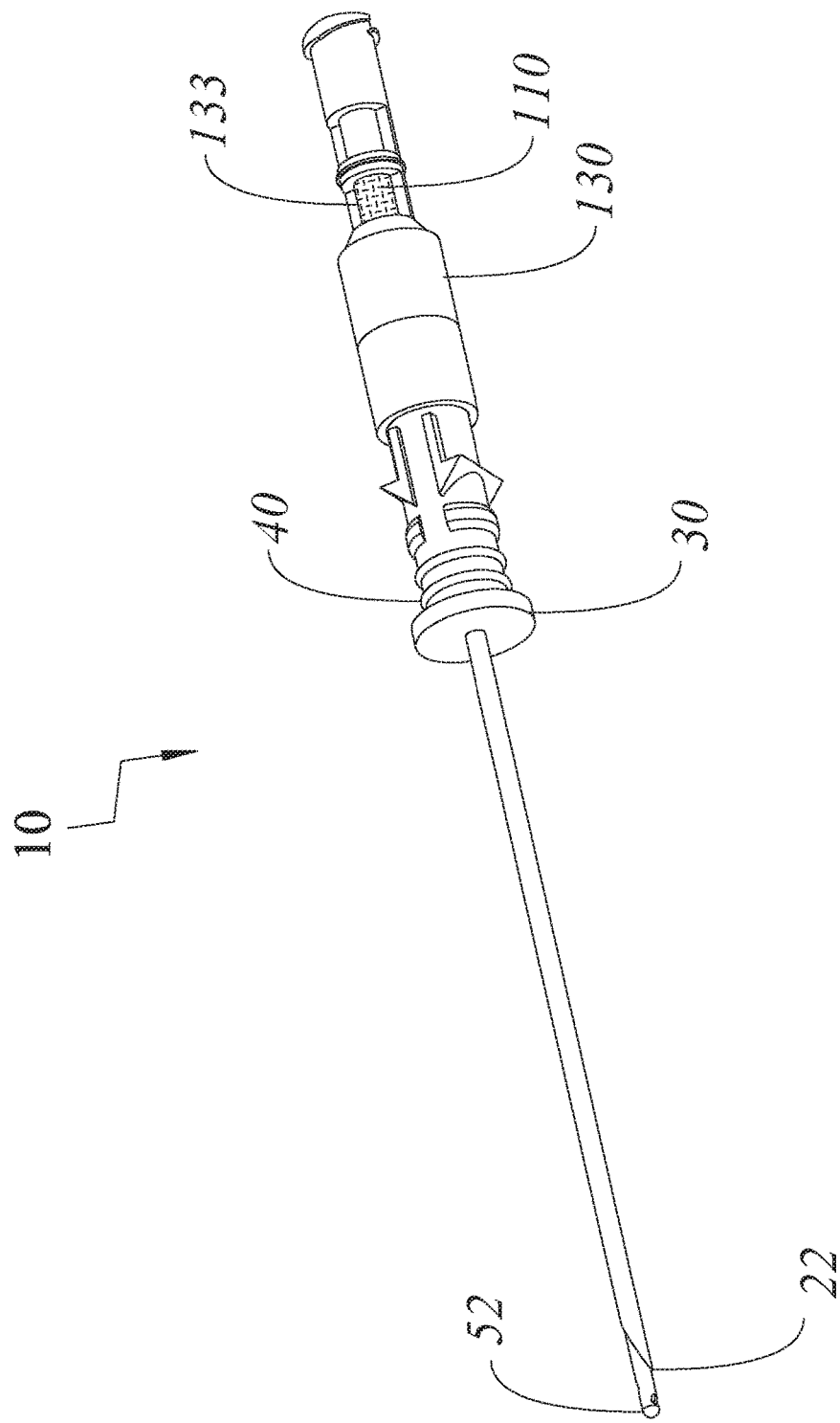
FIG. 12 is a perspective view of a tension treatment device of the present invention in accordance with one embodiment, as assembled prior to use.
Figure 13:
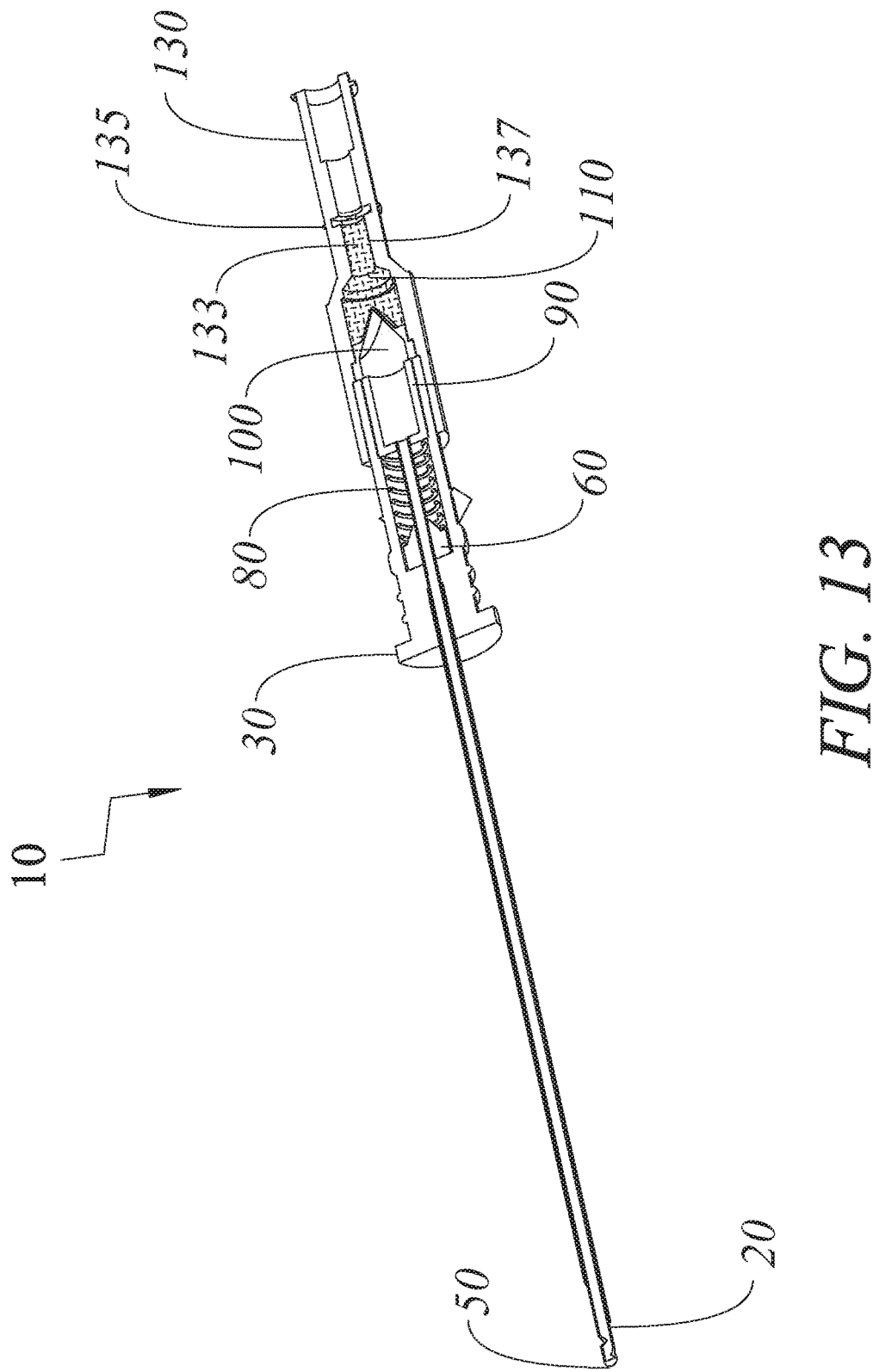
FIG. 13 is a cross section view of a tension treatment device of the present invention in accordance with one embodiment, as assembled prior to use.

Moving now to FIGS. 12 and 13, another embodiment of a device 10 of the present invention device is illustrated. Under this embodiment, pressure documenter or indicator 110 that serves as a means for providing a stable visual indication of whether air has passed proximally through the device is a liquid column (e.g. sterile water, normal saline, or other suitable liquid) that may be colored (e.g. with green dye) or otherwise made easier to see (e.g. containing shiny metallic flecks) such that is easily visible within chamber 133 of cap 130. This documenting liquid 110 can be pre-filled within chamber 133 through check valve 100 to fill line 135, such that it is externally viewable through transparent walls 137 by the user(s). Check valve 100 keeps liquid documenter 110 within cavity 133 and surface tension with walls 137 forces the liquid to remain at line 135. Preferably, a sealing cap (not shown) can be reversibly secured to the distal portion of mating cap 130 to further secure liquid documenter 110 in place during preparation, storage, and/or transport, which is then removed prior to use. Visualization of liquid documenter 110 within cavity 133 stably indicates that air and/or blood has not yet exited the device; that the device is ready to use; and that tension was not present when placed in a patient. The absence of liquid documenter 110, which may be expelled by pressure from device 10, indicates that tension was present.

Figure 14:
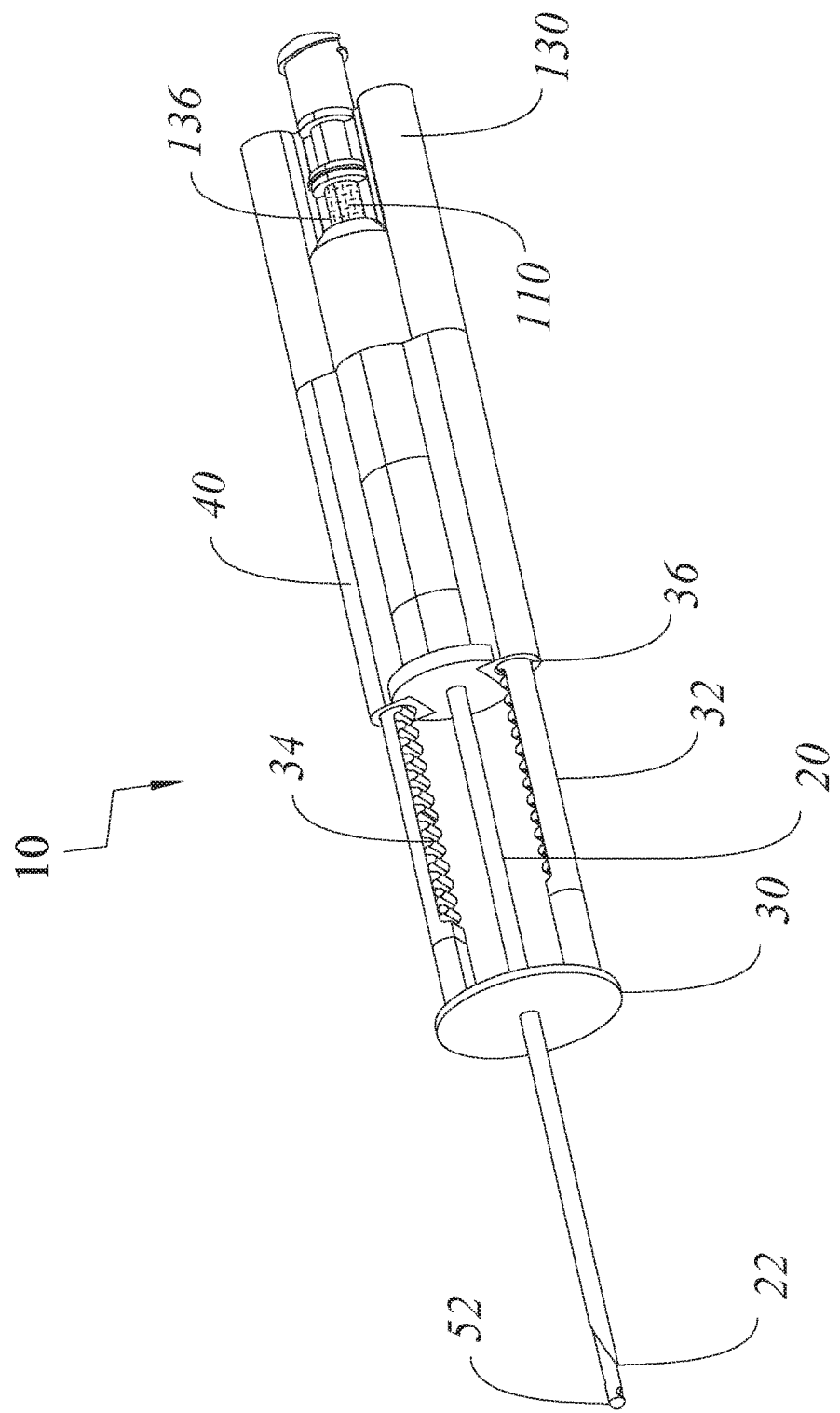
FIG. 14 is a perspective view of a tension treatment device of the present invention in accordance with one embodiment, as assembled prior to use.
Figure 15:
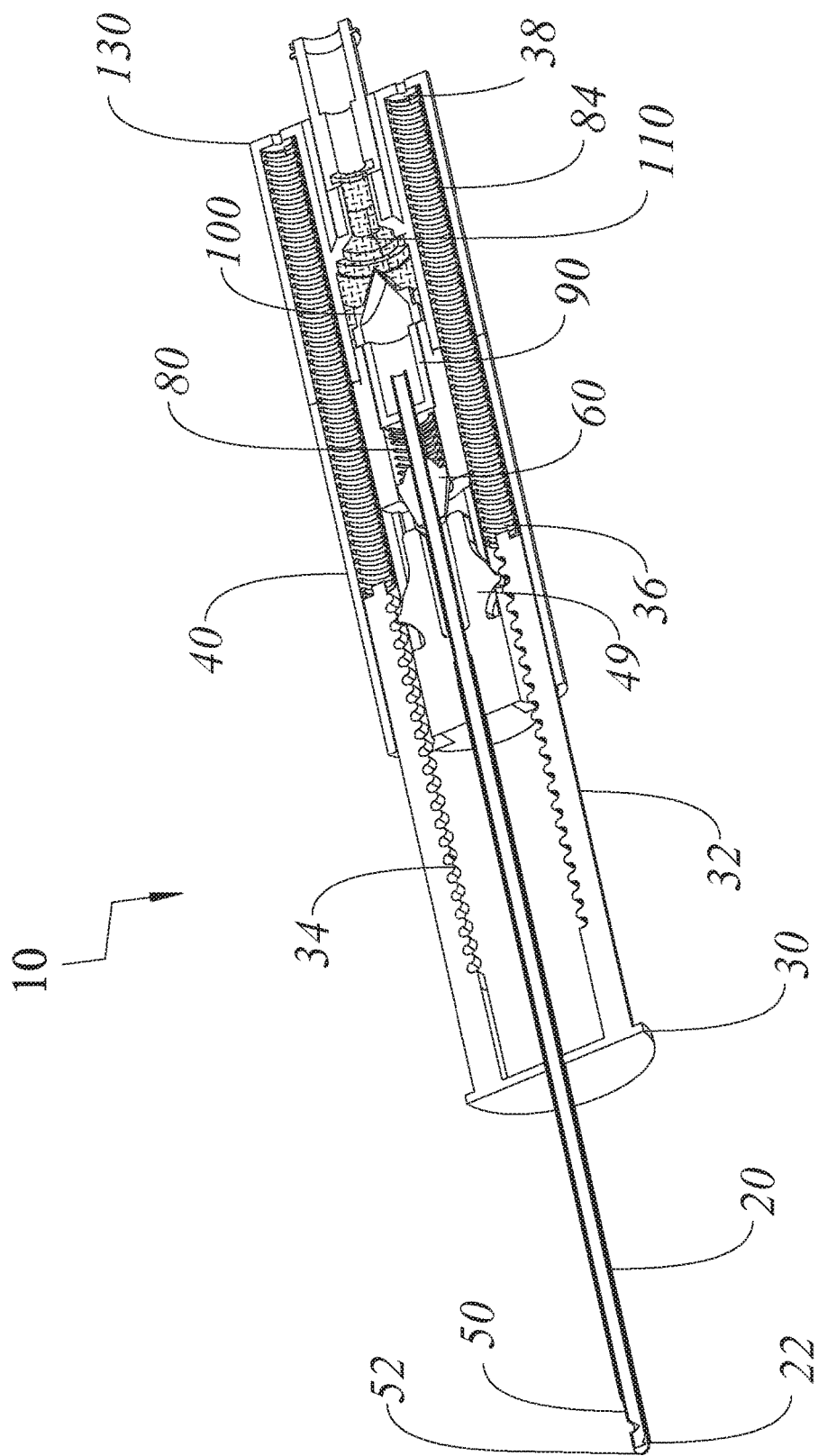
FIG. 15 is a cross section view of a tension treatment device of the present invention in accordance with one embodiment, as assembled prior to use.

Moving now to FIGS. 14 and 15, another embodiment of device 10 of the present invention device is illustrated. Under this embodiment, stabilizer 30 initially extends distally from holder 40 along the tract of needle 20, to provide a mechanism for automatically halting the forward movement of needle tip 22 and probe tip 52 upon penetration into a body cavity (e.g. pleural space). Stabilizer 30 is preferably held in place by one or more rods 32, which extend and preferably lock into the joint tunnel provided by cavities 36 and 38 of holder 40 and cap 130 respectively. These cavities also hold spring 84 which pushes on rod(s) 32 to bias stabilizer 30 distally, although it should be appreciated that other resilient biasing mechanisms could be otherwise utilized (e.g. a piece of elastic or rubber). Holder 40 additionally has one or more phalanges 49 that are resiliently biased medially, but when pushed laterally by probe holder 60 are caused to interact with grooves 34 on rods 32 so as to halt the movement of stabilizer 30 in respect to the rest of device 10.

Figure 16:
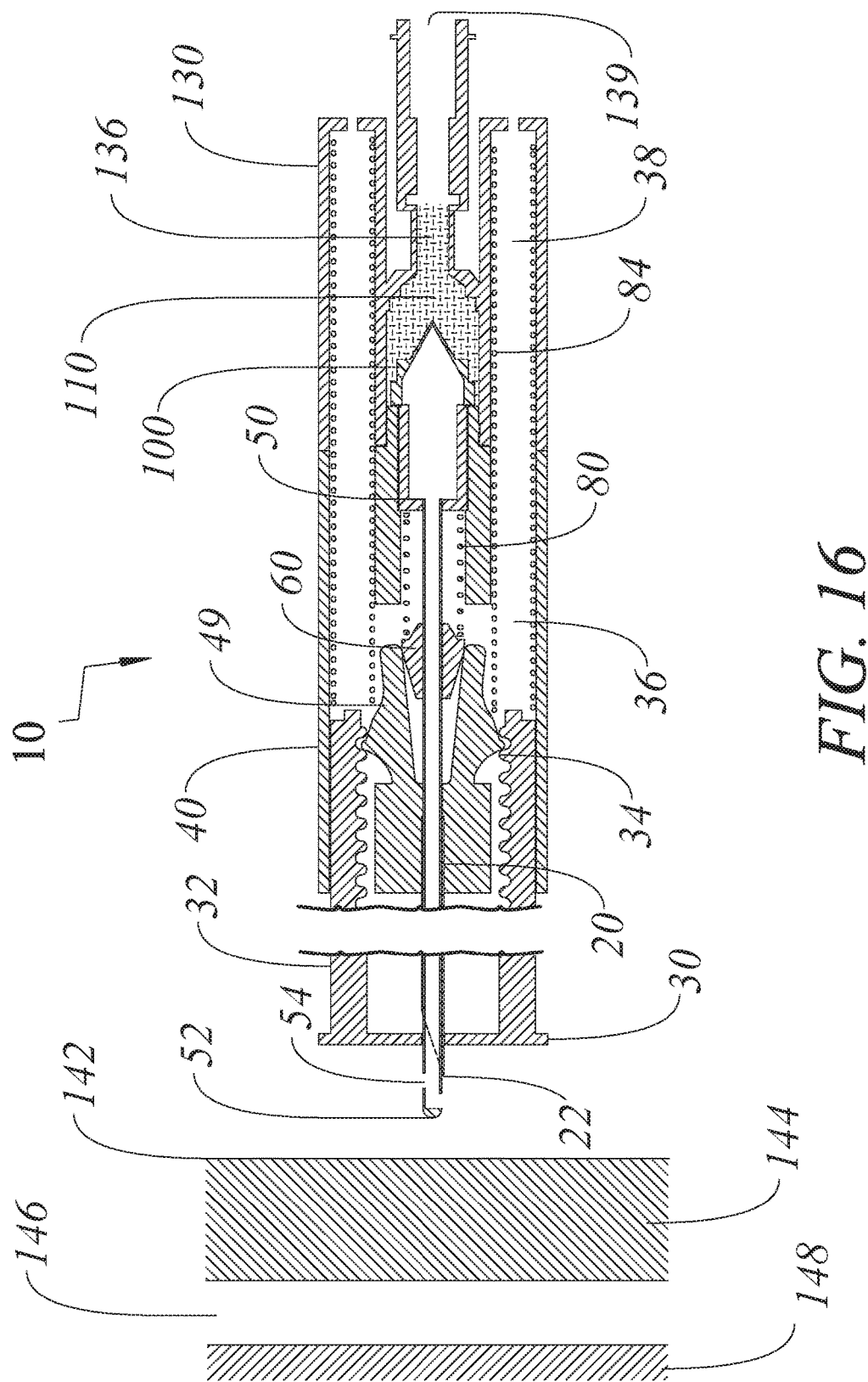
FIG. 16 is a cross-sectional side view of a tension treatment device of the present invention in accordance with one embodiment, shown as assembled prior to insertion into a body cavity.
Figure 17:
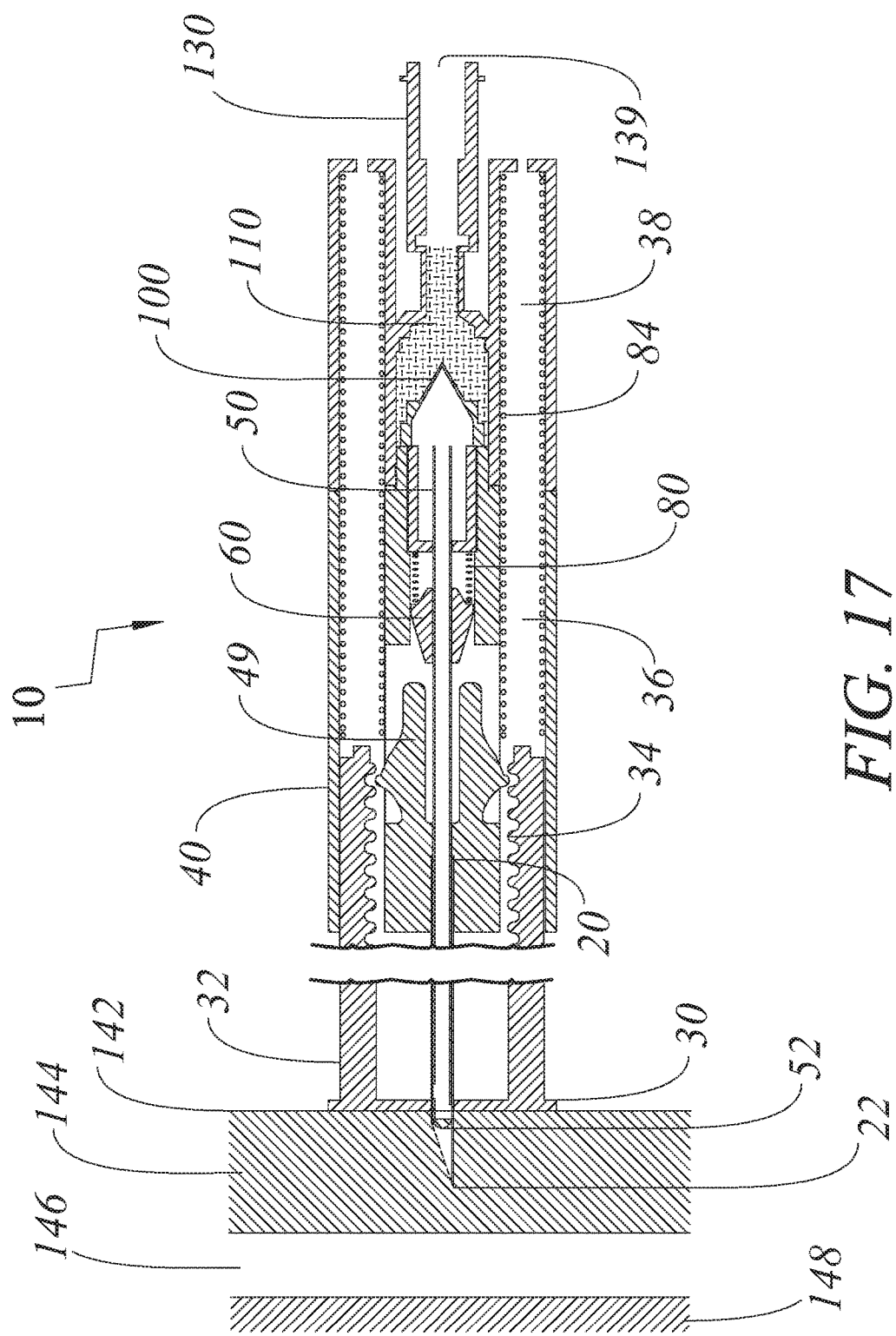
FIG. 17 is a cross-sectional side view of the tension treatment device of FIG. 16, shown upon penetration of the cavity wall (e.g. chest wall).
Figure 18:
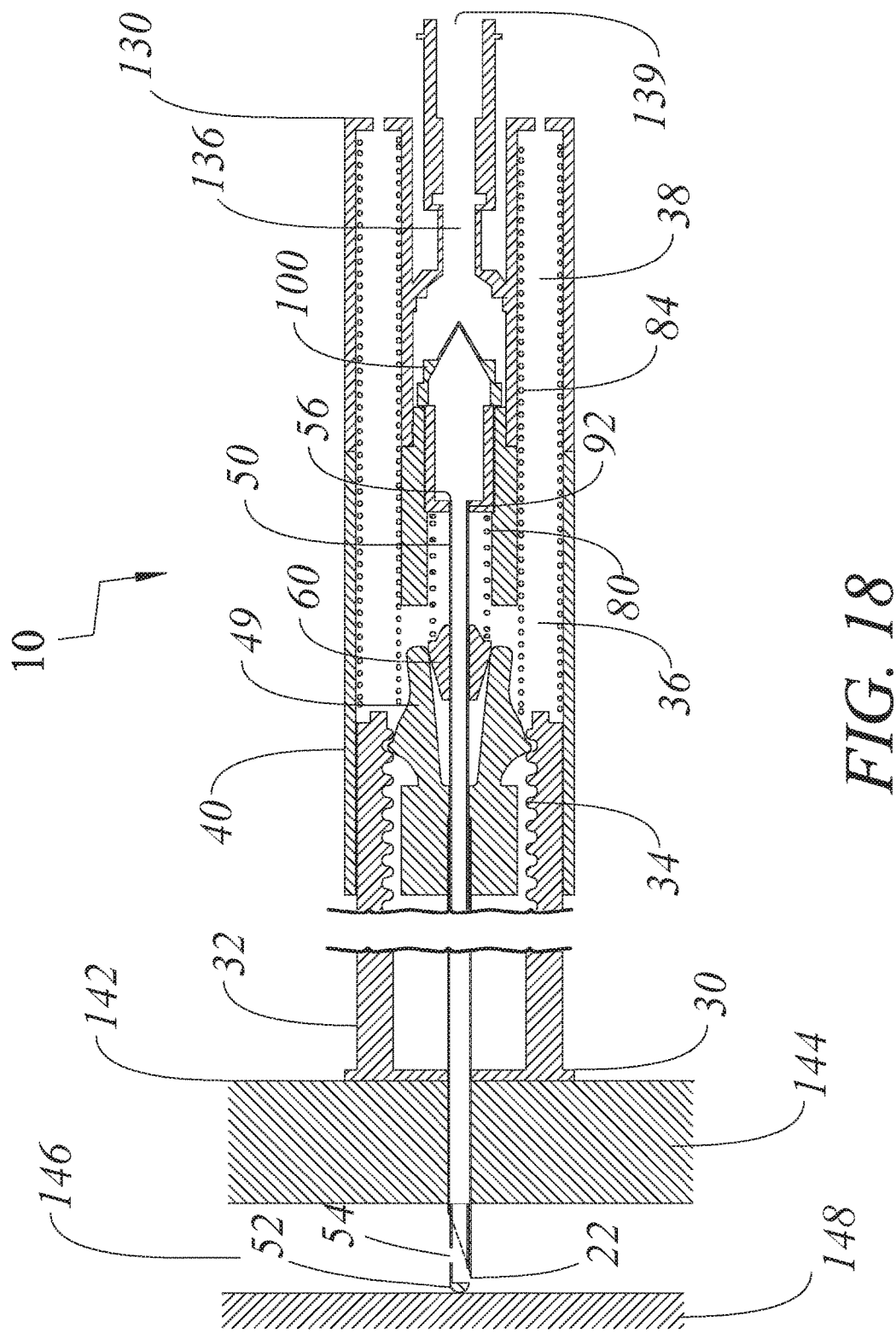
FIG. 18 is a cross-sectional side view of the tension treatment device of FIG. 16, shown upon entrance into the body cavity when there was tension present.

Moving now to FIGS. 16-18, one example mechanism for automatically halting the forward movement of device 10 upon entrance to a body cavity is shown in use. FIG. 16 demonstrates the assembly 10 before insertion into the example of a human body. Biased by spring 80, probe holder 60 is in its distal position, which extends tip 52 of probe 50 out distally from tip 22 of needle 20. Additionally, this pushes phalange(s) 49 laterally to reversibly lock with grooves 34 and inhibit the movement of rod(s) 32 and thus stabilizer 30 in relation to the rest of device 10. Additionally, liquid documenter 110 is present within chamber 136 of mating cap 130, which alerts the user to the device being ready to use.

FIG. 17 demonstrates when needle 20 pierces skin 142 and chest wall 144, which causes probe tip 52 to move proximally in reference to needle tip 22. This causes holder 60 on probe 50 to also move proximally in reference to housing 40. This in turn allows phalanges 49, which are biased medially either through their innate structural design or by other means (e.g. rubber band, spring), to move medially and thus unlock from groove(s) 34 to allow rod 32 and thus stabilizer 30 to move in relation to the rest of device 10. Spring 84 causes stabilizer 30 to be flush with skin 142. Thus, when a general distal biasing of device 10 is provided by the user holding the device (or less preferably by an automatic device mechanism, such as a spring, motor, or elastic band), stabilizer 30 remains flush with skin 142 while the rest of device 10 moves distally, thus inserting needle 20 further into chest wall 142.

FIG. 18 demonstrates device 10 once probe tip 52 and needle tip 22 have reached a body cavity (e.g. in this illustration pleural space 146) which is under tension. Once needle tip 22 enters pleural space 146, spring 80 moves holder 60 distally in reference to housing 40 thus forcing phalange(s) laterally to lock with grooves 34 and inhibit the movement of rod(s) 32 and thus stabilizer 30 in relation to the rest of device 10. This, in turn, prevents needle tip 22 and probe tip 52 from moving further into pleural space 146, thus minimizing the chances of injuring vital structures and moving opening 54 out of the desired body cavity. Under this embodiment, there is an air-tight seal between probe end 56 and cylinder hole 92, which may include the use of an O-ring or other sealing mechanisms. As the pleural cavity 146 was under tension, there is no liquid documenter 110 present within chamber 136 of mating cap 130 as it was expelled when air left the device through opening 139, which stably alerts the current and future user that the patient had tension and may require further care.

There have been illustrated and described herein needle assemblies for the diagnosis and treatment of tension pneumothorax and/or hemothorax. While particular embodiments of the invention have been described, it is not intended that the invention be limited thereto, as it is intended that the invention be as broad in scope as the art will allow and that the specification be read likewise.

Thus, for example, while a spring 80 was disclosed as providing a biasing mechanism for the probe, it will be appreciated that other resilient biasing mechanisms could be utilized. For example, a piece of elastic or rubber (with a hole for fluid communication) could be extended over the rear of the probe and be anchored at a more distal location to provide the forward biasing for the probe. It will be appreciated by those skilled in the art that such use may require simple adjustments to the structure of housing 40, probe 50, holder 60, and/or cylinder 90.

Additionally, while a duck bill valve was described as one embodiment of automatic check valve 100, it will be appreciated that other automatic check valves could be utilized, including a flapper check valve, ball in socket check valve, umbrella check valve, v-tip needle check valve, and/or other automatic check valve. Additionally, more than one check valve may be utilized. It will be appreciated by those skilled in the art that such use may require simple adjustments to the structure of housing 40, probe 50, holder 60, cylinder 90, documenter 110, and/or mating cap 130. It will also be appreciated that in lieu of an automatic check valve, an automatic valve having a pressure threshold could be utilized.

Additionally, while a check valve 100 was described as distal to documenter 110, it will be appreciated that this order could be reversed and/or more than one valve could be utilized. It will be appreciated by those skilled in the art that such use may require simple adjustments to the structure of housing 40, probe 50, holder 60, cylinder 90, valve 100, documenter 110, and/or mating cap 130.

Additionally, while a particular mechanism of using cavity 136 and/or ridges 138 was described as an embodiment for securing documenter 110 is in its initial distal position within cap 130 and preventing its return once deployed, it will be appreciated that other mechanisms could be utilized. In other embodiments, such means include other arrangements of one or more ridges 138, resilient biasing methods such as a spring, other tapering or molding of the inner wall of cavity 136, a pressure valve, slots, locking mechanisms, and/or other means to achieve such goal. Additionally, under different embodiments such means may be arranged to provide various degrees of pressure needed to move documenter 110 proximally (e.g. near minimal pressure above the external environment, slight pressure, increased pressure) as determined most beneficial for function. It will be appreciated by those skilled in the art that such use may require simple adjustments to the structure of cylinder 90, valve 100, documenter 110, and/or mating cap 130.

Additionally, while a particular documenter mechanism 110 was described for providing a visual documentation as to the presence of tension, it will be appreciated that other mechanisms for providing a visual indication could be utilized. The documenter could be of other materials and shapes, could be more distal or proximal within the housing arrangement, and could be viewed through a visually opaque material or partially exposed, among other changes. It will be appreciated by those skilled in the art that such use may require simple adjustments to needle assembly 10.

Additionally, while documenter mechanism 110 was disclosed as providing a mechanism for stably documenting the presence of increased pressure, it will be appreciated that any type of relief valve or other mechanism that provides stable documentation of a release of pressure could be utilized. For example, documenter 110 may be more than one color (e.g. green and red) so as to provide a visual indicator of both a lack of tension (e.g. green) in addition to positive tension (e.g. red) depending on its position. Under related embodiments, indicator 110 may be forced to move in a direction not directly in line with the force of the releasing pressure (e.g. perpendicular). It will be appreciated by those skilled in the art that such use may require simple adjustments to needle assembly 10.

Furthermore, it will be appreciated by those skilled in the art that walls of cap 130 can be all or partially transparent; in other shapes and material; could have other holes or slots; or could have no direct external holes. Additionally, cap 130 may have a luer lock, other syringe fittings, ports, 3-way stopcock, or connections to suction and/or drainage tubing that can serve as the exit for air and/or fluid and/or provide the ability to hook up device 10 to a syringe, suction, and/or other types of drains or tubing. It will be appreciated by those skilled in the art that such use may require simple adjustments to mating cap 130.

Furthermore, it will be appreciated by those skilled in the art that the opening(s) 54 in the distal end 52 of the probe can be arranged in different arrangements so as to best achieves the results herein desired. There may be one, two, three, or more openings, which can be arranged in parallel, staggered, or other fashion and may or may not include a partial or full opening at the most distal tip. These may be arranged as radial slots which are parallel the longitudinal axis of the probe 50, on opposite sides of the probe 50 to be offset longitudinally, or as otherwise arranged. Additionally, in an alternative embodiment needle 20 may also have additional distal openings to facilitate flow of air and/or fluid.

Furthermore, it will be appreciated by those skilled in the art that while a particular mechanism was described for automatically halting the forward movement of the device upon penetration into a body cavity (e.g. pleural space), other mechanisms could be utilized. This includes other mechanisms that use the movement of probe 50 in relation to needle 20, as well as mechanisms that do not utilize this movement (e.g. a mechanical clutch-based needle insertion device). Other embodiments include mechanisms so that rod(s) 32 within cavities 36 and 38 can only move one-way; to lock rod(s) 32 (and probe tip 52) in place before start, once reaching the desired cavity to prevent dislodgement, and/or after use to prevent needle sticks; and other arrangements so as to best achieves the results herein desired. Additionally, phalange(s) 49 may be separate part(s) (e.g. made plastic, rubber, metal, or other desired material); may come directly off of probe holder 60 or probe 50 so as only to deploy when in the distal position; may be a string and pulley system affixed within holder 40; or may be any other system that reversibly locks stabilizer 30 in place when the probe 50 is more distal in comparison to housing 40. Rod(s) 32 may have other types of grooves 34 or mechanisms to reversibly lock with phalanges 49. Additionally, rod(s) 32 may be medially located in reference to phalange(s) 49, so that the mechanism is reversed and that an adjusted probe holder 60 could provide medial pressure to phalange(s) 49 to cause a reversible locking with grooves 32.

Furthermore, it will be appreciated by those skilled in the art that while a particular body cavity (i.e. pleural space) was described, the device and/or mechanism for automatically halting the forward movement of the device upon penetration into a body cavity can be used on other types of potential spaces and body cavities. Examples include the abdominal cavity, trachea, skull and other bones, vessels, bladder and other hollow organs, as well as abscesses and other collections of fluid (e.g. empyema, ascites, and pleural and other effusions).

Furthermore, it will be appreciated by those skilled in the art that the needle assembly 10 of the invention may be used in conjunction with one or more springs and/or resiliently biasing mechanisms, so as to provide a hyper-sensitive detection mechanism to detect the lung, in a manner similar disclosed in U.S. Pat. No. 6,447,483 to Steube, et al which is hereby incorporated by reference herein.

Furthermore, it will be appreciated by those skilled in the art that needle assembly 10 of the invention may be used in conjunction with a catheter, in a manner similar to those disclosed in U.S. Pat. No. 7,229,433 to Mullen, which is hereby incorporated by reference herein. A flexible catheter, with or without an automatic check valve, could be included over needle 20, so that the catheter could remain in the patient if so desired upon removal of the rest of the needle assembly. This catheter could be similar to a standard catheter, Penrose drain, pigtail catheter, chest tube, tracheostomy tube, endotracheal tube, venous or arterial catheter, thoracentesis tube, paracentesis tube, abscess drainage or other medical tube or catheter for placement into a body cavity.

Furthermore, it will be appreciated by those skilled in the art that needle assembly 10 of the invention may be used in conjunction with a stent and/or otherwise expandable tubing or catheter, which may be reversibly or non-reversibly expanded by balloon or other mechanism. Once entering the desired body cavity with the needle assembly 10, this balloon, stent, and/or tubing may serve to push tissue away from needle 20 and/or once expanded function as a standard catheter, Penrose drain, pigtail catheter, chest tube, tracheostomy tube, endotracheal tube, venous or arterial catheter, thoracentesis tube, paracentesis tube, abscess drainage or other medical tube or catheter for placement into a body cavity.

Furthermore, it will be appreciated by those skilled in the art that needle assembly 10 of the invention with simple adjustments may be used for thoracentesis; thoracostomy; paracentesis; arthrocentesis; tracheostomy; laparoscopy; laparotomy; lumbar puncture; cricothyroidotomy; abscess drainage and/or empyema drainage; central venous catheter, peripheral venous catheter, arterial catheter placement; ventriculostomy; or any medical procedure draining air and/or fluid and/or placing a catheter into a body cavity, hollow organ, vessel, and/or potential space.

Furthermore, while parts of embodiments of the needle assembly were described as having certain shapes, and being made of certain materials, it will be appreciated that other materials and shapes can be utilized. It will therefore be appreciated by those skilled in the art that yet other modifications could be made to the provided invention without deviating from its spirit and scope as so claimed.

The following references are hereby incorporated by reference: Mabry et al. "Prehospital advances in the management of severe penetrating trauma." Crit Care Med 2008 Vol. 36, No. 7 (Suppl.); (Harke H T, Pearse L A, Levy A D, et al.: Chest wall thickness in military personnel: Implications for thoracentesis in tension pneumothorax. Mil Med 2007; 172:12:1260-1263); Leigh-Smith et al. "Tension pneumothorax—time for a re-think?" Emerg Med J 2005; "Tactical Combat Casualty Care Guidelines." Military Health System. U.S. Department of Defense. 8 Aug. 2011; Bassett E D et al. "Design of a Mechanical Clutch-Based Needle-Insertion Device." PNAS Early Edition. Aug. 25, 2008. www.pnas.org/cgi/doi/10.1073/pnas.0808274106; and Maxwell W B. "The Hanging Drop to Locate the Pleural Space: A Safer Method for Decompression of Suspected Tension Pneumothorax?" The Journal of Trauma, Injury, Infection, and Critical Care. October 2010.

The invention claimed is:

1. A method for inserting a needle assembly into a body cavity of a patient, the needle assembly including a generally hollow needle having a sharp distal end and a probe having a blunt distal end slidably disposed within the generally hollow needle, the blunt distal end of the probe being biased into a position distal to the sharp distal end, the method comprising:
  engaging the blunt distal end of the probe with the skin and/or other tissue of the patient to overcome the bias to move the probe proximally relative to the hollow needle to cause the sharp distal end of the hollow needle to pierce the skin and/or other tissue of the patient;
  inserting the generally hollow needle into a body cavity of the patient;
  causing the generally hollow needle to automatically halt distal movement into the body cavity upon entry of a distal portion of the generally hollow needle into the body cavity,
  wherein the generally hollow needle automatically halts moving distally into the body cavity upon entry into the body cavity due to the blunt distal end of the probe returning to the position distal to the sharp distal end of the hollow needle upon entry into the body cavity.

2. The method of claim 1, wherein the probe, when in the distally biased position relative to the generally hollow needle, causes a stabilizer configured to stabilize on the skin of the patient to be non-mobile relative to the housing.

3. The method of claim 1, further comprising inserting a catheter into the patient generally simultaneously with the generally hollow needle.

4. The method of claim 1, wherein inserting the generally hollow needle causes a catheter over the generally hollow needle to be inserted into the patient, and further comprising leaving the catheter in the patient and removing the generally hollow needle.

5. The method of claim 1, wherein an expandable tubing is disposed over the generally hollow needle.

6. The method of claim 1, wherein a flow path is formed through the needle assembly, the flow path connecting the body cavity to an external environment.

7. The method of claim 6, wherein the flow path allows for only one-way direction of flow of gas and/or fluid.

8. The method of claim 6, wherein a pressure indicator provides indication of whether gas and/or fluid has passed through the needle assembly.

9. The method of claim 6, wherein gas and/or fluid is released through the needle assembly to connect the body cavity to the external environment.

10. The method of claim 1, wherein the method generally simultaneously treats and documents tension pneumothorax and/or hemothorax.

11. The method of claim 1, further comprising stabilizing the needle assembly against the patient's skin after inserting the needle assembly into the patient.

* * * * *